US007868149B2

(12) United States Patent
Boukharov et al.

(10) Patent No.: US 7,868,149 B2
(45) Date of Patent: Jan. 11, 2011

(54) PLANT GENOME SEQUENCE AND USES THEREOF

(75) Inventors: Andrey A. Boukharov, Chesterfield, MO (US); Yongwei Cao, Lexington, MA (US); David K. Kovalic, University City, MO (US); Jingdong Liu, Ballwin, MO (US); James McIninch, Burlington, MA (US); Wei Wu, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 37 days.

(21) Appl. No.: 11/491,125

(22) Filed: Jul. 24, 2006

(65) Prior Publication Data
US 2007/0039076 A1 Feb. 15, 2007

Related U.S. Application Data

(63) Continuation of application No. 09/620,392, filed on Jul. 19, 2000, now abandoned.

(60) Provisional application No. 60/144,351, filed on Jul. 20, 1999, provisional application No. 60/163,469, filed on Nov. 1, 1999.

(51) Int. Cl.
C07H 21/04 (2006.01)
C12Q 1/08 (2006.01)
(52) U.S. Cl. .................... 536/23.1; 435/6; 536/23.2
(58) Field of Classification Search .................. None
See application file for complete search history.

(56) References Cited

U.S. PATENT DOCUMENTS

| | | | |
|---|---|---|---|
| 4,784,949 A | 11/1988 | Gelfand et al. | |
| 4,956,282 A | 9/1990 | Goodman et al. | |
| 5,011,912 A | 4/1991 | Hopp et al. | |
| 6,093,545 A | 7/2000 | Goodearl et al. | |

FOREIGN PATENT DOCUMENTS

WO  WO 00/18922  4/2000

OTHER PUBLICATIONS

"Revision History for BAF30287," printed from <http://www.ncbi.nlm.nih.gov/entrez/sutils/girevhist.cgi?val=BAF30287&log$=seqview> on Mar. 1, 2009.*
Database sequence GenBank U93559, printed on May 28, 2009 from http://www.ncbi.nlm.nih.gov/nuccore/1935917.*
Jeong et al. Korean J. Biolo. Sc. vol. 1, pp. 135-142, 1997.*
U.S. Appl. No. 09/815,254, filed Mar. 23, 2001, Boukharov et al.
U.S. Appl. No. 10/425,114, filed Mar. 28, 2003, Liu et al.
U.S. Appl. No. 11/329,175, filed Jan. 11, 2006, CaJacob et al.
U.S. Appl. No. 11/329,160, filed Jan. 11, 2006, Bhat et al.
U.S. Appl. No. 11/329,388, filed Jan. 11, 2006, Andersen et al.
U.S. Appl. No. 11/330,082, filed Jan. 12, 2006, Buehler et al.
U.S. Appl. No. 11/330,083, filed Jan. 12, 2006, Byrum et al.
U.S. Appl. No. 11/330,364, filed Jan. 12, 2006, Abad et al.
U.S. Appl. No. 11/331,019, filed Jan. 13, 2006, Fincher et al.
U.S. Appl. No. 11/331,032, filed Jan. 13, 2006, Fincher et al.
U.S. Appl. No. 11/352,295, filed Feb. 13, 2006, Andersen et al.
U.S. Appl. No. 11/353,150, filed Feb. 14, 2006, Andersen et al.
U.S. Appl. No. 11/486,299, filed Jul. 14, 2006, Byrum.
U.S. Appl. No. 11/490,207, filed Jul. 21, 2006, Brown et al.
U.S. Appl. No. 11/491,178, filed Jul. 24, 2006, Hinkle et al.
U.S. Appl. No. 11/491,371, filed Jul. 24, 2006, Byrum.
U.S. Appl. No. 11/497,489, filed Aug. 2, 2006, Byrum et al.
U.S. Appl. No. 11/503,243, filed Aug. 14, 2006, Kovalic et al.
U.S. Appl. No. 11/520,715, filed Sep. 14, 2006, Liu et al..
U.S. Appl. No. 11/521,349, filed Sep. 15, 2006, Byrum et al.
U.S. Appl. No. 11/595,983, filed Nov. 13, 2006, Boukharov et al.
AA501409, EST Database (Aug. 19, 1997).
Aach et al., "*ent*-Kaurene Biosynthesis in a Cell-Free System From Wheat (*Triticum aestivum* L.) Seedlings and the Localisation of *ent*-Kaurene Synthetase in Plastids of Three Species", *Planta* 197(2), 333-342 (1995).
Adams et al., "Complementary DNA Sequencing: Expressed Sequence Tags and Human Genome Project", *Science* 252(5013), 1651-1656 (1991).
Ait-Ali et al., "The *LS* Locus of Pea Encodes the Gibberellin Biosynthesis Enzyme *ent*-Kaurene Synthase A", *Plant J.* 11(3), 443-454 (1997).
Anaviev et al., "Oat-Maize Chromosome Addition Lines: A New System for Mapping the Maize Genome", *Proc. Natl. Acad. Sci. USA* 94, 3524-3529 (1997).
Anton et al., "Sequencing and Overexpression of the *Escherichia coli aroE* Gene Encoding Shikimate Dehydrogenase", *Biochem. J.* 249, 319-326 (1988).
Attwood, "The Babel of Bioinoformatics", *Science* 290(5491), 471-473 (2000).
Bentley, "The Shikimate Pathway—A Metabolic Tree with Many Branches," *Critical Rev. Biochem. Mol. Biol.* 25(5), 307-384 (1990).
Birkenbihl et al., "Cosmid-Derived Map of *E.coli* Strain BHE2600 in Comparison to the Map of Strain W3110", *Nucleic Acids Res.* 17(13), 5057-5069 (1989).
Bishop et al., "The Tomato *Dwarf* Gene Isolated by Heterologous Transposon Tagging Encodes the First Member of a New Cytochrome P450 Family", *Plant Cell* 8, 959-969 (1996).

(Continued)

*Primary Examiner*—Shubo (Joe) Zhou
(74) *Attorney, Agent, or Firm*—Matthew L. Madsen; Ying-Horng Liu; Arnold & Porter LLP

(57) ABSTRACT

The present invention is in the field of plant biochemistry and genetics. More specifically the invention relates to nucleic acid molecules from plant cells, in particular, genomic DNA sequences from rice plants and nucleic acid molecules that contain markers, in particular, single nucleotide polymorphism (SNP) and repetitive element markers. In addition, the present invention provides nucleic acid molecules having regulatory elements or encoding proteins or fragments thereof. The invention also relates to proteins and fragments of proteins so encoded and antibodies capable of binding the proteins. The invention also relates to methods of using the nucleic acid molecules, markers, repetitive elements and fragments of repetitive elements, regulatory elements, proteins and fragments of proteins, and antibodies, for example for genome mapping, gene identification and analysis, plant breeding, preparation of constructs for use in plant gene expression, and transgenic plants.

20 Claims, No Drawings

OTHER PUBLICATIONS

Bonner et al., "Cloning of cDNA Encoding the Bifunctional Dehydroquinase-Shikimate Dehydrogenease of Aromatic-Amino-Acid Biosynthesis in *Nicotiana tabacum*", *Biochem J.* 362, 11-14 (1994).
Bork, "Powers and Pitfalls in Sequence Analysis: The 70% Hurdle", *Genome Res.*, 10, 398-400 (2000).
Bougri et al., "Members of a Low-Copy Number Gene Family Encoding Glutamyl-tRNA Reductase are Differentially Expressed in Barley," *Plant J.* 9(6), 867-878 (1996).
Broun et al., "Catalytic Plasticity of Fatty Acid Modification Enzymes Underlying Chemical Diversity of Plant Lipids", *Science* 282, 1315-1317 (1998).
Bukanov et al., "Ordered Cosmid Library and High-Resolution Physical-Genetic Aap of *Helicobacter pylori* Strain NCTC11638", *Mol. Microbiol.* 11(3), 509-523 (1994).
Charles et al., "Isolation, Characterization and Nucleotide Sequences of the *aroC* Genes encoding Chorismate Synthase from *Salmonella typhi* and *Escherichia coli*", *J. Gen. Microbiol.* 136, 353-358 (1990).
Chen et al., "Microcolinearity in *sh2*-Homologous Regions of the Maize, Rice, and Sorghum Genomes", *Proc. Natl. Acad. Sci. USA* 94, 3431-3435 (1997).
Coulson et al., "Toward a Physical Map of the Genome of the Nematode *Caenorhabditis elegans*", *Proc. Natl. Acad. Sci. USA* 83, 7821-7825 (1986).
Day et al., "Cloning of the cDNA for Glutamyl-tRNA Synthetase from *Arabidopsis thaliana*", *Biochim. Biophys. Acta* 1399(2-3):219-224 (1998).
Duncan et al., "The Overexpression and Complete Amino Acid Sequence of *Escherichia coli* 3-Dehydroquinase", *Biochem. J.* 238, 475-483 (1986).
Eberhard et al., "Cloning and Expression in Yeast of a Higher Plant Chorismate Mutase", *FEBS Lett.* 334(2), 233-236 (1993).
Ebert et al., "Identification of an Essential Upstream Element in the Nopaline Synthase Promoter by Stable and Transient Assays", *Proc. Natl. Acad. Sci. USA* 84(16), 5745-5749 (1987).
Efstratiadis et al., "Enzymatic in Vitro Synthesis of Globin Genes", *Cell* 7, 279-288 (1976).
Eiglmeier et al., "Use of an Ordered Cosmid Library to Deduce the Genomic Organization of *Mycobacterium leprae*", *Mol. Microbiol.* 7(2), 197-206 (1993).
Evans et al., "Immunodetection of Recombinant Proteins Based on Antibodies Directed Against a Metal Binding Peptide Engineered for Purification by Immobilized Metal Affinity Chromatography," *J. Immunol. Meth.* 156(2), 231-238 (1992) (Abstract Only).
Entrez Accession No. M21071 J03227 (Sep. 15, 1989).
Entrez Accession No. 170374 (Sep. 15, 1989).
Entrez Accession No. M27715 (Jun. 15, 1990).
Entrez Accession No. 153878 (Jun. 15, 1990).
Entrez Accession No. X59509 S55160 (Jun. 30, 1993).
Entrez Accession No. 48906 (Jun. 30, 1993).
Entrez Accession No. Y00710 (Sep. 12, 1993).
Entrez Accession No. 40978 (Sep. 12, 1993).
Entrez Accession No. Z26519 (Dec. 2, 1993).
Entrez Accession No. 429153 (Dec. 2, 1993).
Entrez Accession No. 551666 (Jan. 25, 1995).
Entrez Accession No. X81413 (Jan. 25, 1995).
Entrez Accession No. M87280 M99707 (Apr. 12, 1995).
Entrez Accession No. 551855 (Apr. 12, 1995).
Entrez Accession No. 313150 (Jun. 13, 1995).
Entrez Accession No. X73535 (Jun. 13, 1995).
Entrez Accession No. X04306 (Jul. 12, 1995).
Entrez Accession No. 40973 (Jul. 12, 1995).
Entrez Accession No. D63474 D16312 (Jul. 27, 1995).
Entrez Accession No. 474964 (Jul. 27, 1995).
Entrez Accession No. 987267 (Jul. 31, 1995).
Entrez Accession No. U32579 (Sep. 16, 1995).
Entrez Accession No. X82831 (Mar. 1, 1996).
Entrez Accession No. 1213067 (Mar. 1, 1996).
Entrez Accession No. 1220402 (Mar. 5, 1996).
Entrez Accession No. M63245 (Mar. 11, 1996).
Entrez Accession No. W49458 (May 28, 1996).
Entrez Accession No. 1421741 (Oct. 17, 1996).
Entrez Accession No. U54770 (Oct. 18, 1996).
Entrez Accession No. X86101 (Nov. 8, 1996).
Entrez Accession No. 520943 (Feb. 26, 1997).
Entrez Accession No. 2160544 (Jun. 5, 1997).
Entrez Accession No. U63652 (Jun. 6, 1997).
Entrez Accession No. 2257714 (Jul. 15, 1997).
Entrez Accession No. U93215 (Jul. 15, 1997).
Entrez Accession No. 2224890 (Jul. 31, 1997).
Entrez Accession No. 2224892 (Jul. 31, 1997).
Entrez Accession No. U61385 (Aug. 1, 1997).
Entrez Accession No. U61386 (Aug. 1, 1997).
Entrez Accession No. 2316104 (Aug. 8, 1997).
Entrez Accession No. AF010169 (Aug. 9, 1997).
Entrez Accession No. 1524045 (Aug. 20, 1997).
Entrez Accession No. X96943 (Aug. 20, 1997).
Entrez Accession No. Y12809 (Dec. 2, 1997).
Entrez Accession No. D88382 (Mar. 17, 1998).
Entrez Accession No. 3068709 (Apr. 2, 1998).
Entrez Accession No. AF058763 (Aug. 16, 1998).
Entrez Accession No. 3420233 (Apr. 20, 1998).
Entrez Accession No. AF049236 (Apr. 22, 1998).
Entrez Accession No. AF038152 (May 7, 1998).
Entrez Accession No. 2708690 (May 7, 1998).
Entrez Accession No. AC003058 (May 16, 1998).
Entrez Accession No. 3135277 (May 16, 1998).
Entrez Accession No. 3288821 (Jul. 20, 1998).
Entrez Accession No. AF063901 (Jul. 21, 1998).
Entrez Accession No. 3435196 (Sep. 21, 1998).
Entrez Accession No. AF067773 (Sep. 22, 1998).
Entrez Accession No. 3694811 (Sep. 24, 1998).
Entrez Accession No. AJ225107 (Oct. 1, 1998).
Entrez Accession No. 3093410 (Oct. 1, 1998).
Entrez Accession No. AF060481 (Oct. 4, 1998).
Entrez Accession No. 3925407 (Nov. 24, 1998).
Entrez Accession No. AF083948 (Nov. 25, 1998).
Entrez Accession No. AB015492 (Dec. 11, 1998).
Entrez Accession No. 4001680 (Dec. 11, 1998).
Entrez Accession No. AF017431 (Jan. 2, 1999).
Entrez Accession No. 3080490 (Jan. 12, 1999).
Entrez Accession No. AL022602 (Jan. 12, 1999).
Entrez Accession No. AB011416 (Feb. 5, 1999).
Entrez Accession No. AAC17095 GI:315616 (Apr. 5, 1999).
Entrez Accession No. AP000836; GI:6539551 (Aug. 12, 2000).
Entrez Accession No. AY013245 (May 7, 2002).
Fiedler et al., "The Formation of Homogentisate in the Biosynthesis of Tocopherol and Plastoquinone in Spinach Chloroplasts", *Planta* 155, 511-515 (1982).
Garbe et al., "The *Mycobacterium tuberculosis* Shikimate Pathway Genes: Evolutionary Relationship Between Biosynthetic and Catabolic 3-Dehydroquinases", *Mol. Gen. Genet.* 228, 385-392 (1991).
Gasser et al., "Structure, Expression, and Evolution of the 5-Enolpyruvylshikimate-3-Phosphate Synthase Genes of Petunia and Tomato", *J. Biol. Chem.* 263, 4280-4289 (1988).
Gaubier et al., "A Chlorophyll Synthetase Gene from *Arabidopsis thaliana*", *Mol. Gen. Genet.* 249, 58-64 (1995).
GenBank Accession No. U03774 (Jun. 22, 1994).
GenBank Accession No. L37750 (Aug. 3, 1995).
GenBank Accession No. H30177 (Aug. 16, 1995).
GenBank Accession No. W21756 (May 6, 1996).
GenBank Accession No. X80265 (Feb. 26, 1997).
GenBank Accession No. E03435 (Sep. 29, 1997).
GenBank Accession No. AF015462 (Jul. 16, 1998).
Genbank Accession No. AC005922 (Nov. 14, 1998).
GenBank Accession No. X74737 (Jan. 21, 1999).
GenBank Accession No. AU033328 (Apr. 28, 1999).
GenBank Accession No. AQ402486 (Mar. 13, 1999).
GenBank Accession No. AI861202 (Jul. 19, 1999).
GenBank Accession No. AC018632 (Dec. 15, 1999).
GenBank Accession No. AI834598 (Feb. 2, 2000).
GenBank Accession No. AZ134591 (Jun. 2, 2000).
GenBank Accession No. BE428765 (Jul. 26, 2000).
GenBank Accession No. BF542512 (Dec. 11, 2000).

GenBank Accession No. AW871780 (Dec. 11, 2001).
GenBank Accession No. BQ603510 (Jun. 24, 2002).
GenBank Accession No. DR37H4T (Nov. 22, 2002).
GenBank Accession No. BX513761 (May 27, 2003).
GenEMBL Accession No. AF096555 (Jul. 22, 1999).
GenEMBL Accession No. AL096768 (Dec. 12, 1999).
GenSeq Accession No. AAZ35275 (Mar. 27, 2000).
Gerhold et al., "It's the genes! EST access to human genome content", *BioEssays* 18(2), 973-981 (1996).
Gibson et al., "The Bacteriochlorophyll Biosynthesis Gene, bchM, of *Rhodobacter sphaeroides* Encodes S-Adenosyl-1-Methionine: Mg Protoporphyrin IX Methyltransferase", *FEBS Lett*. 352, 127-130 (1994).
Goers et al., "The Differential Allosteric Regulation of Two Chorismate-Mutase Isoenzymes of *Nicotiana silvestris*", *Planta* 162, 117-124 (1984).
Goff, "Rice as a Model for Cereal Genomics", *Curr. Opin. Plant Biol*. 2, 86-89 (1999).
Hedden et al., "Gibberellin Biosynthesis: Enzymes, Genes and Their Regulation", *Annu. Rev. Plant Physiol. Plant Mol. Biol*. 48, 431-460 (1997).
Herrmann, "The Shikimate Pathway as an Entry to Aromatic Secondary Metabolism," *Plant Physiol*. 107, 7-12 (1995).
Hong, "A Rapid and Accurate Strategy for Rice Contig Map Construction by Combination of Fingerprinting and Hybridization", *Plant Mol. Biol*. 35,129-133 (1997).
Hundle et al., "Functional Assignment of *Erwinia herbicola* Eho10 Carotenoid Genes Expressed in *Escherichia coli*", *Mol. Gen. Genet*. 245, 406-416 (1994).
Ibba, "Biochemistry and Bioinformatics: When Worlds Collide," *Trends in Biochem. Sci*. 27(2), 64 (2000).
Iyer et al., "*Quod erat demonstrandum*? The Mystery of Experimental Validation of Apparently Erroneous Computational Analysis of Protein Aequences", *Genome Biol*. 2(12), 1-11 (2001).
Johnston et al., "Cloning and Characterization of Potato cDNAs Involved in Tetrapyrrole Biosynthesis: Ferrochelatase (Accession No. AJ005802), Chloroplatic Protoporphyrinogen IX Oxidase (Accession No. AJ225107), and Mitochondrial Protoporphyrinogen IX Oxidase (Accession No. AJ225108)", *Plant Physiol*. 118, 329-331 (1998).
Keon et al., "Isolation and Heterologous Expression of a Gene Encoding 4-Hydroxyphenylpyruvate Dioxygenase from the Wheat Leaf-Spot Pathogen, *Mycosphaerella graminicola*", *FEMS Microbiol. Lett*. 161, 337-343 (1998).
Kidwell et al., "Transposable Elements as Sources of Variation in Animals and Plants", *Proc. Natl. Acad. Sci. USA* 94, 7704-7711 (1997).
Kim et al., "Construction and Characterization of a Human Bacterial Artificial Chromosome Library", *Genomics* 34, 213-218 (1996).
Knott et al., "Randomly Picked Cosmid Clones Overlap the *pyr*B and *ori*C gap in the Physical Map of the *E. coli* Chromosome", *Nucleic Acids Res*. 16, 2601-2612 (1988).
Ko et al, "An 'Equalized cDNA' Library by the Reassociation of Short Double-Stranded cDNAs", *Nucleic Acids Res*. 18(19), 5705-5711 (1990).
Kyrpides et al., "Whole-Genome Sequence Annotation: 'Going Wrong With Confidence'", *Mol. Microbiol*. 32, 886-887 (1999).
Kurata et al., "A 300 Kilobase Interval Genetic Map of Rice Including 883 Expressed Sequences," *Nature Gen*. 8(4), 362-372 (1994).
Lange et al., "Cloning and Expression of a Gibberellin 2β,3β-Hydroxylase cDNA from Pumpkin Endosperm," *Plant Cell* 9(8), 1459-1467 (1997).
Lange "Cloning Gibberellin Dioxygenase Genes from Pumpkin Endosperm by Heterologous Expression of Enzyme Activities in *Escherichia coli*", *Proc. Natl. Acad. Sci. USA* 94(12), 6553-6558 (1997).
Lange et al., "Expression Cloning of a Gibberellin 20-Oxidase, a Multifunctional Enzyme Involved in Gibberellin Biosynthesis", *Proc. Natl. Acad. Sci. USA* 91(18), 8552-8556 (1994).
Liepman et al., "Sequence Analysis of a cDNA Encoding Alanine:Glyoxylate Amino Transferase from *Arabidopsis* (Accession No. AF063901)", *Plant Physiol*. 117, 1125-1127 (1998).

Lim et al., "Porphobilinogen Deaminase is Encoded by a Single Gene in *Arabidopsis thaliana* and Is Targeted to the Chloroplasts," *Plant Mol. Biol*. 26, 863-872 (1994).
Mahairas et al., "Sequence-Tagged Connectors: A Sequence Approach to Mapping and Scanning the Human Genome", *Proc. Natl. Acad. Sci. USA* 96, 9739-9744 (1999).
Martin et al., "MYB Transcription Factors in Plants", *Trends Genet*. 13(2), 67-73 (1997).
Martin et al., "Mendel's Dwarfing Gene: cDNAs from the *Le* Alleles and Function of the Expressed Proteins", *Proc. Natl. Acad. Sci. USA*, 94(16):8907-8911 (1997).
McCombie et al.,"*Caenorhabditis elegans* Expressed Sequence Tags Identify Gene Families and Disease Gene Homologues," *Nature Gen*. 1, 124-131 (1992).
Meinkoth et al., "Hybridization of Nucleic Acids Immobilized on Solid Supports", *Anal. Biochem*. 138, 267-284 (1984).
Mende et al., "The Geranylgeranyl Diphosphate Synthase Gene of *Gibberella fujikuroi*: Isolation and Expression", *Mol. Gen. Genet*. 255(1), 96-105 (1997).
Mohan et al., "Genome Mapping, Molecular Markers and Marker-Assisted Selection Crop Plants", *Mol. Breed*. 3, 87-103 (1997).
Nakane et al., "Nucleotide Sequence of the Shikimate Kinase Gene (*arol*) of *Bacillus subtilis*", *J. Ferment. Bioeng*. 77, 312-314 (1994).
Nakayashiki et al., "Nucleotide Sequence of a cDNA Clone Encoding Glutamyl-tRNA Reductase from Rice (Accession No. AB011416)", *Plant Physiol*. 117, 332 (1998).
NCBI Accession No. S42508 (May 8, 1993).
NCBI Accession No. D23883 (Nov. 29, 1993).
NCBI Accession No. AAA34069, corresponding to gi:535771 (Sep. 11, 1994).
Norris et al., "Complementation of the *Arabidopsis pds 1* Mutation with the Gene Encoding *p*-Hydroxyphenylpuruvate Dioxygenase", *Plant Physiol*. 117, 1317-1323 (1998).
Oka et al., "Replication Origin of the *Escherichia coli* K-12 Chromosome: The Size and Structure of the Minimum DNA Segment Carrying the Information for Autonomous Replication", *Mol. Gen. Genet*. 178(1), 9-20 (1980).
Okubo et al., "Large Scale cDNA Sequencing for Analysis of Quantitative and Qualitative Aspects of Gene Expression", *Nature Gen*. 2, 173-179 (1992).
Phillips et al., "Isolation and Expression of Three Gibberellin 20-Oxidase cDNA Clones from *Arabidopsis*", *Plant Physiol*. 108(3), 1049-1057 (1995).
Porra, "Recent Progress in Porphyrin and Chlorophyll Biosynthesis", *Photochem. Photobiol*. 65(3), 492-516 (1997).
Russell et al., "Structural Features can be Unconserved in Proteins with Similar Folds. An Analysis of Side-Chain to Side-Chain Contacts Secondary Structure and Accessibility", *J. Mol. Biol*. 244, 332-350 (1994).
Sakamoto et al., "An Overview of Gibberellin Metabolism Enzyme Genes and Their Related Mutants in Rice", *Plant Physiol*. 134, 1642-1653 (2004).
Schmitz et al., "The Tomato *Blind* Gene Encodes a MYB Transcription Factor that Controls the Formation of Lateral Meristems", *Proc. Nat. Acad. Sci*. 99(2), 1064-1069 (2002).
Schünmann et al., "Identification of Three cDNA Clones Expressed in the Leaf Extension Zone and with Altered Patterns of Expression in the *Slender* Mutant of Barley: A Tonoplast Intrinsic Protein, a Putative Structural Protein and Protochlorophylide Oxidoreductase," *Plant Mol. Biol*. 31, 529-537 (1996).
Seffernick et al., "Melamine Deaminase and Atrazine Chlorohydrolase: 98 Percent Identical but Functionally Different", *J. Bacteriol*. 183(8), 2405-2410 (2001).
Sigma Chemical Catalogue (Sigma Chemical Co.; P.O. Box 14508, St. Louis MO 63178) 1993, product Nos. 01256, 03628, 04375, pp. 736-737.
Smith et al., "Partial Purification and Characterization of the Gibberellin $A_{20}$ 3β-Hydroxylase from Seeds of *Phaseolus vulgaris*", *Plant Physiol*. 94:1390-1401 (1990).
Smith et al., "The First Step of Gibberellin Biosynthesis in Pumpkin is Catalyzed by at Least Two Copalyl Diphosphate Synthases Encoded by Differentially Regulated Genes", *Plant Physiol*. 118, 1411-1419 (1998).

Stammers et al., "Rapid Purification and Characterization of HIV-1 Reverse Transcriptase and RNaseH Engineered to Incorporate a C-terminal Tripeptide α-Tubulin Epitope", *FEBS Lett.* 283(2), 298-302 (1991).

Tanaka et al., "The Third Member of the *hemA* gene Family Encoding Glutamyl-tRNA Reductase is Primarily Expressed in Roots in *Hordeum vulgare*", *Photosynthesis Res.* 53, 161-171 (1997).

Tanksley et al., "Chromosome landing: a paradigm for map-based gene cloning in plants with large genomes", *Trends in Genet.* 11(2), 63-68 (1995).

Tikhonov et al., "Colinearity and its Exceptions in Orthologous *adh* Regions of Maize and *Sorghum*", *Proc. Natl. Acad. Sci. USA* 96, 7409-7414 (1999).

van de Loo et al., "An Oleate 12-Hydroxylase from *Ricirus communis* L. is a Fatty Acyl Desaturase Homolog", *Proc. Nat. Acad. Sci.* 92, 6743-6747 (1995).

Venter et al., "A New Strategy for Genome Sequencing", *Nature* 381, 364-366 (1996).

Venter et al., "The Sequence of the Human Genome" *Science* 291, 1304-1351 (2001).

Wang et al., "Construction of a Rice Bacterial Artificial Chromosome Library and Identification of Clones Linked to the Xa-21 Disease Resistance Locus", *Plant J.* 7(3), 525-533 (1995).

Wells et al., "The Chemokine Information Source: Identification and Characterization of Novel Chemokines Using the WorldWideWeb and Expressed Sequence Tag Databases", *J. Leukocyte Biol.* 61(5), 545-550 (1997).

Wendel et al., "New Isozyme Systems for Maize (*Zea mays* L.): Aconitate Hydratase, Adenylate Kinase, NADH Dehydrogenase, and Shikimate Dehydrogenase", *Biochem. Genet.* 26(5-6), 421-446 (1988) (Abstract Only).

Wenzel et al., "Physical mapping of the *Mycoplasma pneumoniae* genome", *Nucleic Acids Res.* 16(17), 8323-8336 (1988).

Winkler et al., "The Maize *Dwarf3* Gene Encodes a Cytochrome P450-Mediated Early Step in Gibberellin Biosynthesis", *Plant Cell* 7(8), 1307-1317 (1995).

Woese et al., "Conservation of Primary Structure in 16S Ribosomal RNA", *Nature* 254, 83-85 (1975).

Yomo et al., "Histochemical Studies on Protease Formation in the Cotyledons of Germinating Bean Seeds," *Planta* 112(1), 35-43 (1973).

Zhang et al., "Physical Mapping of the Rice Genome with BACs", *Plant Mol. Biol.* 35, 115-127 (1997).

Zhang et al., "Construction and Characterization of Two Rice Bacterial Artificial Chromosome Libraries from the Parents of a Permanent Recombinant Inbred Mapping Population", *Mol. Breeding* 2, 11-24 (1996).

Zwick et al., "Physical Mapping of the *liguleless* Linkage Group in *Sorghum bicolor* Using Rice RFLP-Selected *Sorghum* BACs", *Genetics* 248, 1983-1992 (1998).

Christensen et al., "Regulation of Auxin Response by the Protein Kinase PINOID," Cell, 100:469-478 (2000).

Nozue et al., "A Phytochrome from the Fern Adiantum with Features of the Putative Photoreceptor NPH1," Proc. Natl. Acad. Sci. USA, 95:15826-15830 (1998).

Lawton et al., "Molecular Cloning of Plant Transcripts Encoding Protein Kinase Homologs," Proc. Natl. Acad. Sci. USA, 86:3140-3144 (1989).

Lin et al., "Differential Accumulation of Transcripts Encoding Protein Kinase Homologs in Greening Pea Seedlings," Proc. Natl. Acad. Sci. USA, 88:6951-6955 (1991).

Abstract of Khanna et al., "Photoregulated Expression of the PsPK3 and PsPK5 Genes in Pea Seedlings," Plant Mol. Biol. 39(2):231-242 (1999).

Abstract of Chono et al., "Characterization of a Protein Kinase Gene Responsive to Auxin and Gibberellin in Cucumber Hypocotyls," Plant Cell Physiol., 39(9):958-967 (1998).

GenBank Accession No. AAB54117 (May 12, 1997).
GenBank Accession No. AAC26704 (Mar. 11, 2002).
GenBank Accession No. AAB95304 (Feb. 27, 2002).
GenBank Accession No. CAA66616 (Nov. 14, 2006).
GenBank Accession No. AAD34696 (Jun. 2, 1999).
GenBank Accession No. AAB71418 (Sep. 29, 1997).
GenBank Accession No. BAA82168 (Jul. 3, 1999).
GenBank Accession No. AAC78477 (Nov. 19, 1998).
GenBank Accession No. BAA36192 (Mar. 15, 2002).
GenBank Accession No. CAA82993 (Apr. 18, 2005).

* cited by examiner

PLANT GENOME SEQUENCE AND USES THEREOF

CROSS REFERENCE TO RELATED APPLICATION

This application is a continuation of U.S. application Ser. No. 09/620,392 filed Jul. 19, 2000, now abandoned, which claims priority under 35 U.S.C. §119(e) to U.S. Application Ser. No. 60/144,351 filed Jul. 20, 1999, and to U.S. Application Ser. No. 60/163,469 filed Nov. 1, 1999, each of which is herein incorporated by reference in its entirety.

INCORPORATION OF SEQUENCE LISTING

This application contains a sequence listing, which is contained on three identical CD-Rs: two copies of the sequence listing (COPY 1 REPLACEMENT Oct. 18, 2006 and COPY 2 REPLACEMENT Oct. 18, 2006) and a sequence listing in Computer Readable Form (CRF), all of which are herein incorporated by reference. All three sequence listing CD-Rs each contain one file called "pa_00300.rpt" which is 462,735,360 bytes in size (measured in Windows XP) and which was created on Oct. 18, 2006.

FIELD OF THE INVENTION

The present invention is in the field of plant biochemistry and genetics. More specifically the invention relates to nucleic acid molecules from plant cells, in particular, genomic DNA sequences from *Oryza sativa* (rice) plants and nucleic acid molecules that contain markers, in particular, single nucleotide polymorphism (SNP) and repetitive element markers. In addition, the present invention provides nucleic acid molecules having regulatory elements or encoding proteins or fragments thereof. The invention also relates to proteins and fragments of proteins so encoded and antibodies capable of binding the proteins. The invention also relates to methods of using the nucleic acid molecules, markers, repetitive elements and fragments of repetitive elements, regulatory elements, proteins and fragments of proteins, and antibodies, for example for genome mapping, gene identification and analysis, plant breeding, preparation of constructs for use in plant gene expression, and transgenic plants.

BACKGROUND OF THE INVENTION

I. Rice

Rice is one of three cereals produced annually at worldwide levels of approximately half a billion tons and more than 90% of produced rice is for human consumption (Goff S. A. *Curr. Opin. Plant Biol.* 2:86-89 (1999), the entirety of which is herein incorporated by reference). Rice, however, is not only a commercially important crop, it is also a model for other cereal crops. The identification in *Oryza sativa* (rice) of proteins, genetic and physical markers, biological agents such as plant promoters, open reading frames, plant gene intron regions, plant gene intron/exon junctions, and regulatory elements, etc., is important in the development of nutritionally enhanced or agriculturally enhanced crops, in particular cereal crops. Such agents are useful in, for example, marker development, genetic mapping or linkage analysis, marker assisted breeding, physical genome mapping, transgenic crop production, crop monitoring diagnostics, antibody production and gene modification. Such agents can also have pharmaceutical or nutriceutical applications.

Rice can be used as a model for other cereal genomes because it has a genome size smaller than the other major cereals. The size of the rice genome is estimated at 420 to 450 megabase pairs. Sorghum, maize, barley and wheat have larger genomes (1000, 3000, 5000 and 16000 Mpb respectively). The smaller genome size of rice results in a higher gene density relative to the other cereals. Based on estimates of 30,000 genes in a cereal genome, rice will have on average one gene approximately every 15 Kbp. Similarly, maize and wheat have one gene approximately every 100 and 500 kpb, respectively. It has been reported that this higher gene density in rice makes it a target for cereal gene discovery efforts and genomic sequence analysis (Goff S. A *Curr. Opin. Plant Biol.* 2:86-89 (1999), the entirety of which is herein incorporated by reference). Although the genes in rice are present at a higher relative density than in other cereals, they are predicted to be arranged in a similar general order within the genome (Goff S. A *Curr. Opin. Plant Biol.* 2:86-89 (1999)). Comparisons of the physical and genetic maps of cereal genomes have lead to reports that colinearity of gene order exists among the various cereal genomes studied.

In addition to the general conservation of gene order among the cereals, studies of a number of individual genes demonstrate that there is also considerable homology among various cereal gene families. This conservation of gene and protein sequence suggests that studies on the functions of genes or proteins from one cereal could lead to the elucidation of the functions of orthologous genes/proteins in other cereals. Non-coding regulatory regions of the genome may also retain similar function between the various cereals. For example, strong constitutive or tissue-specific promoters from one cereal are likely to retain function when introduced as a portion of a transgene in another species (Goff S. A *Curr. Opin. Plant Biol.* 2:86-89 (1999).

II. Sequence Comparisons

Genome sequence information from rice allows comparisons of rice sequences with other rice sequences as well as with those of other flowering plant genome sequences, particularly other cereal plant species, and also with genome sequences and gene sequences from other organisms, including bacteria, humans, and yeast. Such information provides valuable insights into the translation of plant genetic information into a flowering plant and also reveals genetic differences involved in the differentiation of the plant kingdom. In addition, genome sequencing and mapping provides increased opportunities for identification and isolation of agents associated with plant traits, as well as insight into mechanisms of genome interactions.

Rice sequences can be compared, for example, to sequences that encode promoters or proteins or other sequences. These homologies can be determined by similarity searches (Adams et al., *Science* 252:1651-1656 (1991), the entirety of which is herein incorporated by reference).

A characteristic feature of a DNA sequence is that it can be compared with other DNA sequences. Sequence comparisons can be undertaken by determining the similarity of the test or query sequence with sequences in publicly available or propriety databases ("similarity analysis") or by searching for certain motifs ("intrinsic sequence analysis") (e.g., cis elements) (Coulson, *Trends in Biotechnology*, 12:76-80 (1994); Birren et al., Genome Analysis, 1:543-559 (1997), both of which are herein incorporated by reference in their entirety).

Similarity analysis includes database search and alignment. Examples of public databases include the DNA Database of Japan (DDBJ) (on the Worldwide web at ddbj.nig.acjp/); GENBANK® (on the Worldwide web at ncbi.nlm.nih.gov/web/Genbank/Index.html); and the European Molecular Biology Laboratory Nucleic Acid Sequence Database (EMBL) (on the Worldwide web at ebi.ac.uk/ebi_docs/embl_db.html). A number of different search algorithms have been developed, one example of which is the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, *Trends in Biotechnology*, 12:76-80 (1994); Birren, et al., *Genome Analysis*, 1:543-559 (1997)).

BLASTN takes a nucleotide sequence (the query sequence) and its reverse complement and searches them against a nucleotide sequence database. BLASTN was designed for speed, not maximum sensitivity, and may not find distantly related coding sequences. BLASTX takes a nucleotide sequence, translates it in three forward reading frames and three reverse complement reading frames, and then compares the six translations against a protein sequence database. BLASTX is useful for sensitive analysis of preliminary (single-pass) sequence data and is tolerant of sequencing errors (Gish and States, *Nature Genetics*, 3:266-272 (1993), the entirety of which is herein incorporated by reference).

Given a coding nucleotide sequence and the protein it encodes, it is often preferable to use the protein as the query sequence to search a database because of the greatly increased sensitivity to detect more subtle relationships. This is due to the larger alphabet of proteins (20 amino acids) compared with the alphabet of nucleic acid sequences (4 bases), where it is far easier to obtain a match by chance. In addition, with nucleotide alignments, only a match (positive score) or a mismatch (negative score) is obtained, but with proteins, the presence of conservative amino acid substitutions can be taken into account. Here, a mismatch may yield a positive score if the non-identical residue has physical/chemical properties similar to the one it replaced. Various scoring matrices are used to supply the substitution scores of all possible amino acid pairs. A general purpose scoring system is the BLOSUM62 matrix (Henikoff and Henikoff, *Proteins*, 17:49-61 (1993), the entirety of which is herein incorporated by reference), which is currently the default choice for BLAST programs. BLOSUM62 is tailored for alignments of moderately diverged sequences and thus may not yield the best results under all conditions. Altschul, *J. Mol. Biol.* 36:290-300 (1993), the entirety of which is herein incorporated by reference, uses a combination of three matrices to cover all contingencies. This may improve sensitivity, but at the expense of slower searches. In practice, a single BLOSUM62 matrix is often used but others (PAM40 and PAM250) may be attempted when additional analysis is necessary. Low PAM matrices are directed at detecting very strong but localized sequence similarities, whereas high PAM matrices are directed at detecting long but weak alignments between very distantly related sequences.

Homologues in other organisms are available that can be used for comparative sequence analysis. Multiple alignments are performed to study similarities and differences in a group of related sequences. CLUSTAL W is a multiple sequence alignment package available that performs progressive multiple sequence alignments based on the method of Feng and Doolittle, *J. Mol. Evol.* 25:351-360 (1987), the entirety of which is herein incorporated by reference. Each pair of sequences is aligned and the distance between each pair is calculated; from this distance matrix, a guide tree is calculated, and all of the sequences are progressively aligned based on this tree. A feature of the program is its sensitivity to the effect of gaps on the alignment; gap penalties are varied to encourage the insertion of gaps in probable loop regions instead of in the middle of structured regions. Users can specify gap penalties, choose between a number of scoring matrices, or supply their own scoring matrix for both the pairwise alignments and the multiple alignments. CLUSTAL W for UNIX and VMS systems is available at: ftp.ebi.ac.uk. Another program is MACAW (Schuler et al., *Proteins, Struct. Func. Genet*, 9:180-190 (1991), the entirety of which is herein incorporated by reference, for which both Macintosh and Microsoft Windows versions are available. MACAW uses a graphical interface, provides a choice of several alignment algorithms, and is available by anonymous ftp at: ncbi.nlm.nih.gov (directory/pub/macaw).

Sequence motifs are derived from multiple alignments and can be used to examine individual sequences or an entire database for subtle patterns. With motifs, it is sometimes possible to detect distant relationships that may not be demonstrable based on comparisons of primary sequences alone. Currently, the largest collection of reported sequence motifs is PROSITE (Bairoch and Bucher, *Nucleic Acid Research*, 22:3583-3589 (1994), the entirety of which is herein incorporated by reference). PROSITE may be accessed via either the ExPASy server on the World Wide Web or anonymous ftp site. Many commercial sequence analysis packages also provide search programs that use PROSITE data.

A resource for searching protein motifs is the BLOCKS E-mail server developed by S. Henikoff, *Trends Biochem Sci.*, 18:267-268 (1993), the entirety of which is herein incorporated by reference; Henikoff and Henikoff, *Nucleic Acid Research*, 19:6565-6572 (1991), the entirety of which is herein incorporated by reference; Henikoff and Henikoff, *Proteins*, 17:49-61 (1993). BLOCKS searches a protein or nucleotide sequence against a database of protein motifs or "blocks." Blocks are defined as short, ungapped multiple alignments that represent highly conserved protein patterns. The blocks themselves are derived from entries in PROSITE as well as other sources. Either a protein or nucleotide query can be submitted to the BLOCKS server; if a nucleotide sequence is submitted, the sequence is translated in all six reading frames and motifs are sought in these conceptual translations. Once the search is completed, the server will return a ranked list of significant matches, along with an alignment of the query sequence to the matched BLOCKS entries.

Conserved protein domains can be represented by two-dimensional matrices, which measure either the frequency or probability of the occurrences of each amino acid residue and deletions or insertions in each position of the domain. This type of model, when used to search against protein databases, is sensitive and usually yields more accurate results than simple motif searches. Two popular implementations of this approach are profile searches (such as GCG program ProfileSearch) and Hidden Markov Models (HMMs) (Krough, et al., *J. Mol. Biol.* 235:1501-1531 (1994); Eddy, *Current Opinion in Structural Biology* 6:361-365 (1996), both of which are herein incorporated by reference in their entirety). In both cases, a large number of common protein domains have been converted into profiles, as present in the PROSITE library, or HHM models, as in the Pfam protein domain library (Sonnhammer, et al., *Proteins* 28:405-420 (1997), the entirety of which is herein incorporated by reference). Pfam contains more than 500 HMM models for enzymes, transcription factors, signal transduction molecules, and structural proteins. Protein databases can be queried with these profiles or HMM models, which will identify proteins containing the domain of interest. For example, HMMSW or HMMFS, two programs in a public domain package called HMMER (Sonnhammer, et al., *Proteins* 28:405-420 (1997)) can be used.

PROSITE and BLOCKS represent collected families of protein motifs. Thus, searching these databases entails submitting a single sequence to determine whether or not that sequence is similar to the members of an established family. Programs working in the opposite direction compare a collection of sequences with individual entries in the protein databases. An example of such a program is the Motif Search Tool, or MoST (Tatusov, et al., *Proc. Natl. Acad. Sci.* 91:12091-12095 (1994), the entirety of which is herein incorporated by reference). On the basis of an aligned set of input sequences, a weight matrix is calculated by using one of four methods (selected by the user); a weight matrix is simply a representation, position by position in an alignment, of how likely a particular amino acid will appear. The calculated weight matrix is then used to search the databases. To increase sensitivity, newly found sequences are added to the original data set, the weight matrix is recalculated, and the search is performed again. This procedure continues until no new sequences are found.

III. Contig Assembly

A characteristic feature of a large scale shotgun sequencing project is that the sequence data can be processed and assembled into contiguous sequences (contigs), which represent a reconstruction of the original genome sequence from the cloned fragments. Likewise, individual Bacterial Artificial Chromosome (BAC) clones within a BAC library can be shot gun sequenced and these data can be assembled into contigs within each clone. Programs are available in the public domain that can analyze the sequence output and assemble the sequences into larger sequence regions representing contiguous sequences of the target genome. Examples of such programs can be found at, for example, on the website genome.wustl.edu/gsc, on the Worldwide web at sanger.ac.uk, and on the Worldwide web at mbt.washington.edu. An example of sequence reading program is Phred (on the Worldwide web at mbt.washington.edu). Phred reads DNA sequencer trace data, calls bases, assigns quality values to the bases, and writes the base calls and quality values to output files.

The process of assembling DNA sequence fragments generally involves three phases; the overlap phase, the layout phase and the multi-alignment, or consensus, phase. In the overlap phase, each fragment is compared against every other fragment to determine if they share a common subsequence, an indication that they were potentially sampled from overlapping stretches of the original DNA strand. Pairs of fragments are compared in two ways; 1) with both fragments in the same relative orientation, and 2) with one of the fragments having been reverse complemented. In the layout phase, a series of alternate assemblies or layouts of the fragments based on the pairwise overlaps is generated. A layout specifies the relative locations and orientations of the fragments with respect to each other and is typically visualized as an arrangement of overlapping directed lines, one for each fragment. The general criterion for the layout phase is to produce plausible assemblies of maximum likelihood. In this manner, it can be determined if there is more than one way to put the pieces together and if different solutions appear equally plausible. In such a case, one would return to the lab and obtain additional information to resolve the ambiguity. The multi-alignment, or consensus, phase uses more information than just the pairwise alignments in the layout. The sequences of all the fragments in a layout are simultaneously aligned, giving a final set of contigs representing regions of the target genome. An example of an assembly program is PHRAP, which can be found at the website chimera.biotech.washington.edu/UWGC/tools/phrap.htm.

IV. Gene Mapping and Marker Assisted Introgression of Plant Traits

Genome sequence information from rice provides markers that will assist in the development of improved plants. Marker assisted introgression of traits into plants have been reported. An initial step in that process is the localization of the trait by gene mapping. Gene mapping is the process of determining a gene's position relative to other genes and genetic markers through linkage analysis. The basic principle for linkage mapping is that the closer together two genes are on the chromosome, the more likely they are to be inherited together (Rothwell, *Understanding Genetics*. $4^{th}$ Ed. Oxford University Press, New York, p. 703 (1988), the entirety of which is herein incorporated by reference). Briefly, a cross is made between two genetically compatible but divergent parents relative to traits under study. Genetic markers are then used to follow the segregation of traits under study in the progeny from the cross (often a backcross, $F_2$, or recombinant inbred population).

Linkage analysis is based on the level at which markers and genes are co-inherited (Rothwell, *Understanding Genetics*. $4^{th}$ Ed. Oxford University Press, New York, p. 703 (1988). Statistical tests like chi-square analysis can be used to test the randomness of segregation or linkage (Kochert, *The Rockefeller Foundation International Program on Rice Biotechnology*, University of Georgia Athens, Ga., pp. 1-14 (1989), the entirety of which is herein incorporated by reference). In linkage mapping, the proportion of recombinant individuals out of the total mapping population provides the information for determining the genetic distance between the loci (Young, *Encyclopedia of Agricultural Science, Vol.* 3, pp. 275-282 (1994), the entirety of which is herein incorporated by reference).

Classical mapping studies utilize easily observable, visible traits instead of molecular markers. These visible traits are also known as naked eye polymorphisms. These traits can be morphological like plant height, fruit size, shape and color or physiological like disease response, photoperiod sensitivity or crop maturity. Visible traits are useful and are still in use because they represent actual phenotypes and are easy to score without any specialized lab equipment. By contrast, the other types of genetic markers are arbitrary loci for use in linkage mapping and often not associated to specific plant phenotypes (Young, *Encyclopedia of Agricultural Science*, Vol. 3, pp. 275-282 (1994). Many morphological markers cause such large effects on phenotype that they are undesirable in breeding programs. Many other visible traits have the disadvantage of being developmentally regulated (i.e., expressed only certain stages; or at specific tissue and organs). Oftentimes, visible traits mask the effects of linked minor genes making it nearly impossible to identify desirable linkages for selection (Tanksley et al., *Biotech.* 7:257-264 (1989), the entirety of which is herein incorporated by reference).

Although a number of important agronomic characters are controlled by loci having major effects on phenotype, many economically important traits, such as yield and some forms of disease resistance, are quantitative in nature. This type of phenotypic variation in a trait is typically characterized by continuous, normal distribution of phenotypic values in a particular population (polygenic traits) (Beckmann and Soller *Oxford Surveys of plant Molecular Biology, Miffen.* (ed.), Vol. 3, Oxford University Press, UK., pp. 196-250 (1986), the entirety of which is herein incorporated by reference). Loci contributing to such genetic variation are often termed, minor genes, as opposed to major genes with large effects that follow a Mendelian pattern of inheritance. Polygenic traits are also predicted to follow a Mendelian type of inheritance, however the contribution of each locus is expressed as an increase or decrease in the final trait value.

The advent of DNA markers, such as restriction fragment length polymorphic markers (RFLPs), microsatellite markers, single nucleotide polymorphic markers (SNPs), and random amplified polymorphic markers (RAPDs), allow the resolution of complex, multigenic traits into their individual Mendelian components (Paterson et al., *Nature* 335:721-726 (1988), the entirety of which is herein incorporated by reference). A number of applications of RFLPs and other markers have been suggested for plant breeding. Among the potential applications for RFLPs and other markers in plant breeding include: varietal identification (Soller and Beckmann, *Theor. Appl. Genet.* 67:25-33 (1983); Tanksley et al., *Biotech.* 7:257-264 (1989), both of which are herein incorporated by reference in their entirety); QTL mapping (Edwards et al., *Genetics* 116:113-115 (1987); Nienhuis et al., *Crop Sci.* 27:797-803 (1987); Osborn et al., *Theor. Appl. Genet.* 73:350-356 (1987); Romero-Severson et al., *Use of RFLPs In Analysis Of Quantitative Trait Loci In Maize*, In Helentjaris and Burr (eds.), pp. 97-102 (1989); Young et al., *Genetics* 120:579-585 (1988); Martin et al., *Science* 243:1725-1728 (1989); Sarfatti et al., *Theor. Appl. Genet.* 78:22-26 (1989); Tanksley et al., *Biotech.* 7:257-264 (1989); Barone et al., *Mol. Gen. Genet.* 224:177-182 (1990); Jung et al., *Theor. Appl. Genet.* 79:663-672 (1990); Keim et al., *Genetics* 126:735-742 (1990); Keim et al., *Theor. Appl. Genet.* 79:465-369 (1990); Paterson et al., *Genetics* 124:735-742 (1990); Martin et al., *Proc. Natl. Acad. Sci. USA* 88:2336-2340 (1991); Messeguer et al., *Theor. Appl. Genet.* 82:529-536 (1991); Michelmore et al., *Proc. Natl. Acad. Sci. USA* 88:9828-9832 (1991); Ottaviano et al., *Theor. Appl. Genet.* 81:713-719 (1991); Yu et al., *Theor. Appl. Genet.* 81:471-476 (1991); Diers et al., *Crop Sci.* 32:377-383 (1992); Diers et al., *Theor. Appl. Genet.* 83:608-612 (1992); *J. Plant Nut.* 15:2127-2136 (1992); Doebley et al., *Proc. Natl. Acad. Sci. USA* 87:9888-9892 (1990), all of which are herein incorporated by reference in their entirety); screening genetic resource strains for useful quantitative trait alleles and introgression of these alleles into commercial varieties (Beckmann and Soller, *Theor. Appl. Genet.* 67:35-43 (1983), the entirety of which is herein incorporated by reference); marker-assisted selection (Tanksley et al., *Biotech.* 7:257-264 (1989)); and map-based cloning (Tanksley et al., *Biotech.* 7:257-264 (1989)). In addition, DNA markers can be used to obtain information about: (1) the number, effect, and chromosomal location of each gene affecting a trait; (2) effects of multiple copies of individual genes (gene dosage); (3) interaction between/among genes controlling a trait (epistasis); (4) whether individual genes affect more than one trait (pleiotropy); and (5) stability of gene function across environments (G×E interactions).

SUMMARY OF THE INVENTION

The present invention provides a substantially purified nucleic acid molecule, the nucleic acid molecule capable of specifically hybridizing to a second nucleic acid molecule having a nucleic acid sequence selected from the group consisting of SEQ ID NO: 1 through SEQ ID NO: 69652 or complements thereof or fragments of either.

The present invention also provides a substantially purified nucleic acid molecule encoding a rice protein or fragment thereof, wherein the rice protein or fragment thereof is encoded by a nucleic acid sequence selected from the group consisting of 69652 1 through SEQ ID NO: 69652 or complements thereof or fragments of either.

The present invention also provides a substantially purified protein or fragment thereof encoded by a first nucleic acid molecule which specifically hybridizes to a second nucleic acid molecule, the second nucleic acid molecule having a nucleic acid sequence selected from the group consisting of SEQ ID NO: 1 through SEQ ID NO: 69652 or complements thereof.

The present invention also provides a substantially purified protein or fragment thereof encoded by a nucleic acid sequence selected from the group consisting of SEQ ID NO: 1 through SEQ ID NO: 69652 or complements thereof or fragments of either.

The present invention also provides a substantially purified antibody or fragment thereof, the antibody or fragment thereof capable of specifically binding to the protein or fragment thereof encoded by a first nucleic acid molecule which specifically hybridizes to a second nucleic acid molecule, the second nucleic acid molecule having a nucleic acid sequence selected from the group consisting of SEQ ID NO: 1 through SEQ ID NO: 69652 or complements thereof or fragment of either.

The present invention also provides a transformed plant having a nucleic acid molecule which comprises: (A) an exogenous promoter region which functions in a plant cell to cause the production of an mRNA molecule; which is linked to (B) a structural nucleic acid molecule, wherein the structural nucleic acid molecule is selected from the group consisting of a protein or fragment thereof encoding sequence located within SEQ ID NO: 1 through SEQ ID NO: 69652 or complements thereof; which is linked to (C) a 3' non-translated sequence that functions in a plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of an mRNA molecule wherein the promoter nucleic acid molecule is selected from the group consisting of SEQ ID NO: 1 through SEQ ID NO: 69652 or complements thereof or fragments of either; which is linked to (B) a structural nucleic acid molecule encoding a protein or fragment thereof; which is linked to (C) a 3' non-translated sequence that functions in a plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of an mRNA molecule; which is linked to (B) a transcribed nucleic acid molecule with a transcribed strand and a non-transcribed strand, wherein the transcribed strand is complementary to a nucleic acid molecule having a nucleic acid sequence selected from the group consisting of SEQ ID NO: 1 through SEQ ID NO: 69652 or complements thereof and the transcribed strand is complementary to an endogenous mRNA molecule; which is linked to (C) a 3' non-translated sequence that functions in plant cells to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of an mRNA molecule wherein the promoter nucleic acid molecule is selected from the group consisting of SEQ ID NO: 1 through SEQ ID NO: 69652 or complements thereof; which is linked to (B) a transcribed nucleic acid molecule with a transcribed strand and a non-transcribed strand, wherein the transcribed strand is complementary to an endogenous mRNA molecule; which is linked to (C) a 3' non-translated sequence that functions in plant cells to cause termination of transcription and addition of polyadenylated ribonucleotides to a 3' end of the mRNA molecule.

The present invention also provides a computer readable medium having recorded thereon one or more nucleic acid molecules encoding a rice protein or fragment thereof, wherein the rice protein or fragment thereof is encoded by a nucleic acid sequence selected from the group consisting of SEQ ID NO: 1 through SEQ ID NO: 69652 or complements thereof or fragments of either.

The present invention also provides a method of introgressing a trait into a plant comprising using a nucleic acid marker for marker assisted selection of the plant, the nucleic acid marker complementary to a nucleic acid sequence selected from the group consisting of SEQ ID NO: 1 through SEQ ID NO: 69652 or complements thereof, and introgressing the trait into a plant.

The present invention also provides a method for screening for a trait comprising interrogating genomic DNA for the presence or absence of a marker molecule that is genetically linked to a nucleic acid sequence complementary to a nucleic acid sequence selected from the group consisting of SEQ ID NO: 1 through SEQ ID NO: 69652 or complements thereof; and detecting the presence or absence of the marker.

The present invention also provides a method for determining the likelihood of the presence or absence of a trait in a plant comprising the steps of: (A) obtaining genomic DNA from the plant; (B) detecting a marker nucleic acid molecule; wherein the marker nucleic acid molecule specifically hybridizes with a nucleic acid sequence that is genetically linked to a nucleic acid sequence complementary to a nucleic acid sequence selected from the group consisting of SEQ ID NO: 1 through SEQ ID NO: 69652 or complements thereof; (C) determining the level, presence or absence of the marker nucleic acid molecule, wherein the level, presence or absence of the marker nucleic acid molecule is indicative of the likely presence in the plant of the trait.

The present invention also provides a method for determining a genomic polymorphism in a plant that is predictive of a trait comprising the steps: (A) incubating a marker nucleic acid molecule, under conditions permitting nucleic acid hybridization, and a complementary nucleic acid molecule obtained from the plant, the marker nucleic acid molecule having a nucleic acid sequence selected from the group consisting of SEQ ID NO: 1 through SEQ ID NO: 69652 or complements thereof or fragments of either; (B) permitting hybridization between the marker nucleic acid molecule and the complementary nucleic acid molecule obtained from the plant; and (C) detecting the presence of the polymorphism.

The present invention also provides a method of determining an association between a polymorphism and a plant trait comprising: (A) hybridizing a nucleic acid molecule specific for the polymorphism to genetic material of a plant, wherein the nucleic acid molecule comprises a nucleic acid sequence selected from the group consisting of SEQ ID NO: 1 through SEQ ID NO: 69652 or complements thereof or fragments of either; and (B) calculating the degree of association between the polymorphism and the plant trait.

The present invention provides a method for isolating a nucleic acid molecule in a non-rice cereal comprising: (A) defining a genomic region of rice by reference to a marker molecule, wherein said marker molecule comprises a nucleic acid sequence selected from the group consisting of SEQ ID NO: 1 through SEQ ID NO: 69652 or complement thereof or fragment of either; (B) identifying a syntenic genomic region of said non-rice cereal that corresponds to said defined genomic region of rice; and (C) isolating said syntenic genomic region of said non-rice cereal that corresponds to said defined genomic region of rice.

The present invention provides a method for isolating a nucleic acid molecule in a cereal comprising: (A) defining a genomic region of rice by reference to a marker molecule, wherein said marker molecule comprises a nucleic acid sequence selected from the group consisting of SEQ ID NO: 1 through SEQ ID NO: 69652 or complement thereof or fragment of either; (B) identifying a syntenic genomic region of said cereal that corresponds to said defined genomic region of rice; and (C) isolating said syntenic genomic region of said cereal that corresponds to said defined genomic region of rice.

The present invention provides a method for interrogating a genomic region of a non-rice cereal comprising interrogating genomic DNA for the presence or absence of two marker molecules, wherein said two marker molecules comprise two nucleic acid sequences selected from the group consisting of SEQ ID NO: 1 through SEQ ID NO: 69652 or complement thereof or fragment of either, and detecting the presence or absence of said two marker molecules.

DETAILED DESCRIPTION OF THE INVENTION

Agents of the Invention (a) Nucleic Acid Molecules

Agents of the present invention include nucleic acid molecules and more specifically BACs or nucleic acid fragment molecules thereof.

Agents of the present invention include plant nucleic acid molecules and more specifically include rice, more preferably *Oryza sativa* L (japonica type), and more preferably *Oryza sativa* L (japonica type), cv. Nipponbare. A subset of the nucleic acid molecules of the present invention includes nucleic acid molecules that are marker molecules. Another subset of the nucleic molecules of the present invention includes nucleic acid molecules that are promoters and/or regulatory elements. Another subset of the nucleic acid molecules of the present invention includes nucleic acid molecules that encode a gene or fragment thereof. Another subset of the nucleic acid molecules of the present invention encodes proteins or fragments of proteins. In a preferred embodiment the nucleic acid molecules of the present invention are derived from rice, more preferably *Oryza sativa* L (japonica type), and more preferably *Oryza sativa* L (japonica type), cv. Nipponbare.

Fragment nucleic acid molecules may encode significant portion(s) of, or indeed most of, these nucleic acid molecules. For example, a fragment nucleic acid molecule can encode a rice protein or fragment thereof. Alternatively, the fragments may comprise smaller oligonucleotides (having from about 15 to about 400 nucleotide residues, and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

As used herein, an agent, be it a naturally occurring molecule or otherwise may be "sub-stantially purified", if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (e.g., DNA, peptide etc.), that is, or results, however indirect, from human manipulation of a nucleic acid molecule.

It is understood that the agents of the present invention may be labeled with reagents that facilitate detection of the agent (e.g., fluorescent labels (Prober, et al., *Science* 238:336-340 (1987); Albarella et al., EP 144914, chemical labels (Sheldon et al., U.S. Pat. No. 4,582,789; Albarella et al., U.S. Pat. No. 4,563,417, modified bases (Miyoshi et al., EP 119448, all of which are hereby incorporated by reference in their entirety).

It is further understood, that the present invention provides, for example, bacterial, viral, microbial, insect, fungal, algal and plant cells comprising an agent of the present invention.

Nucleic acid molecules or fragment nucleic acid molecules, or BACs or fragments thereof, of the present invention are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning*, A Laboratory Manual, 2nd Ed., Cold Spring Harbor Press, Cold Spring Harbor, N.Y. (1989), and by Haymes et al., *Nucleic Acid Hybridization, A Practical Approach*, IRL Press, Washington, D.C. (1985), both of which are herein incorporated by reference in their entirety. Departures from complete complementarity are therefore permissible, as long as such departures do not completely preclude the capacity of the molecules to form a double-stranded structure. Thus, in order for a nucleic acid molecule, fragment nucleic acid molecule, BAC nucleic acid molecule or fragment BAC nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NO: 1 through SEQ ID NO: 69652 or complements thereof under moderately stringent conditions, for example at about 2.0×SSC and about 40° C.

In a particularly preferred embodiment, a nucleic acid of the present invention will specifically hybridize to one or more of the nucleic acid molecules set forth in SEQ ID NO:1 through SEQ ID NO: 69652 or complements thereof under high stringency conditions. In one aspect of the present invention, the nucleic acid molecules of the present invention have one or more of the nucleic acid sequences set forth in SEQ ID NO: 1 through to SEQ ID NO: 69652 or complements thereof. In another aspect of the present invention, one or more of the nucleic acid molecules of the present invention share between 100% and 90% sequence identity with one or more of the nucleic acid sequences set forth in SEQ ID NO: 1 through to SEQ ID NO: 69652 or complements thereof. In a further aspect of the present invention, one or more of the nucleic acid molecules of the present invention share between 100% and 95% sequence identity with one or more of the nucleic acid sequences set forth in SEQ ID NO: 1 through to SEQ ID NO: 69652 or complements thereof. In a more preferred aspect of the present invention, one or more of the nucleic acid molecules of the present invention share between 100% and 98% sequence identity with one or more of the nucleic acid sequences set forth in SEQ ID NO: 1 through to SEQ ID NO: 69652 or complements thereof. In an even more preferred aspect of the present invention, one or more of the nucleic acid molecules of the present invention share between 100% and 99% sequence identity with one or more of the sequences set forth in SEQ ID NO: 1 through to SEQ ID NO: 69652 or complements thereof. In a further, even more preferred aspect of the present invention, one or more of the nucleic acid molecules of the present invention exhibit 100% sequence identity with one or more nucleic acid molecules present within the genomic library herein designated BAC#OJ (Monsanto Company, St. Louis, Miss., United States of America).

(i) Nucleic Acid Molecule Markers

One aspect of the present invention concerns nucleic acid molecules SEQ ID NO:1 through SEQ ID NO: 69652 or complements thereof and other nucleic acid molecules of the present invention, that contain microsatellites, single nucleotide substitutions (SNPs), repetitive elements or parts of repetitive elements or other markers. Microsatellites typically include a 1-6 nucleotide core element that are tandemly repeated from one to many thousands of times. A different "allele" occurs at an SSR locus as a result of changes in the number of times a core element is repeated, altering the length of the repeat region, (Brown et al., *Methods of Genome Analysis in Plants*, (ed.) Jauhar, CRC Press, Inc, Boca Raton, Fla., USA; London, England, UK, pp. 147-159, (1996), the entirety of which is herein incorporated by reference). SSR loci occur throughout plant genomes, and specific repeat motifs occur at different levels of abundance than those found in animals. The relative frequencies of all SSRs with repeat units of 1-6 nucleotides have been surveyed. The most abundant SSR is AAAAAT followed by $A_n$, $AG_n$ AAT, AAC, AGC, AAG, AATT, AAAT and AC. On average, 1 SSR is found every 21 and 65 kb in dicots and monocots. Fewer CG nucleotides are found in dicots than in monocots. There is no correlation between abundance of SSRs and nuclear DNA content. The abundance of all tri and tetranucleotide SSR combination jointly have been reported to be equivalent to that of the total di-nucleotide combinations. Mono- di- and tetra-nucleotide repeats are all located in noncoding regions of DNA while 57% of those trinucleotide SSRs containing CG were located within gene coding regions. All repeated trinucleotide SSRs composed entirely of AT are found in noncoding regions, (Brown et al., *Methods of Genome Analysis in Plants*, ed. Jauhar, CRC Press, Inc, Boca Raton, Fla., USA; London, England, UK, pp. 147-159 (1996)).

Microsatellites can be observed in SEQ NO:1 to SEQ NO:69652 or complements thereof by using the BLASTN program to examine sequences for the presence/absence of microsatellites. In this system, raw sequence data is searched through databases, which store SSR markers collected from publications and 692 classes of di-, tri and tetranucleotide repeat markers generated by computer. Microsatellites can also be observed by screening the BAC library of the present invention by colony or plaque hybridization with a labeled probe containing microsatellite markers; isolating positive clones and sequencing the inserts of the positive clones; suitable primers flanking the microsatellite markers.

Single nucleotide polymorphisms (SNPs) are single base changes in genomic DNA sequence. They generally occur at greater frequency than other markers and are spaced with a greater uniformity throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a result of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314-331 (1980); Konieczny and Ausubel, *Plant J.* 4:403-410 (1993), both of which are herein incorporated by reference in their entirety), enzymatic and chemical mismatch assays (Myers et al., *Nature* 313:495-498 (1985), the entirety of which is herein incorporated by reference), allele-specific PCR (Newton et al., *Nucl. Acids Res.* 17:2503-2516 (1989); Wu et al., *Proc. Natl. Acad. Sci. USA* 86:2757-2760 (1989), both of which are herein incorporated by reference in their entirety), ligase chain reaction (Barany, *Proc. Natl. Acad. Sci. USA* 88:189-193 (1991), the entirety of which is herein incorporated by reference), single-strand conformation polymorphism analysis (Labrune et al., *Am. J. Hum. Genet.* 48: 1115-1120 (1991), the entirety of which is herein incorporated by reference), primer-directed nucleotide incorporation assays (Kuppuswami et al., *Proc. Natl. Acad. Sci. USA* 88:1143-1147 (1991), the entirety of which is herein incorporated by reference), dideoxy fingerprinting (Sarkar et al., *Genomics* 13:441-443 (1992), the entirety of which is herein incorporated by reference), solid-phase ELISA-based oligonucleotide ligation assays (Nikiforov et al., *Nucl. Acids Res.* 22:4167-4175 (1994), the entirety of which is herein incorporated by reference), oligonucleotide fluorescence-quenching assays (Livak et al., *PCR Methods Appl.* 4:357-362 (1995a), the entirety of which is herein incorporated by reference), 5'-nuclease allele-specific hybridization Taq-Man™ assay (Livak et al., *Nature Genet.* 9:341-342 (1995), the entirety of which is herein incorporated by reference), template-directed dye-terminator incorporation (TDI) assay (Chen and Kwok, *Nucl. Acids Res.* 25:347-353 (1997), the entirety of which is herein incorporated by reference), allele-specific molecular beacon assay (Tyagi et al., *Nature Biotech.* 16: 49-53 (1998), the entirety of which is herein incorporated by reference), PinPoint assay (Haff and Smirnov, *Genome Res.* 7: 378-388 (1997), the entirety of which is herein incorporated by reference), and dCAPS analysis (Neff et al., *Plant J.* 14:387-392 (1998), the entirety of which is herein incorporated by reference).

SNPs can be observed by examining sequences of overlapping clones in the BAC library according to the method described by Taillon-Miller et al. *Genome Res.* 8:748-754 (1998), the entirety of which is herein incorporated by reference. SNPs can also be observed by screening the BAC library of the present invention by colony or plaque hybridization with a labeled probe containing SNP markers; isolating positive clones and sequencing the inserts of the positive clones; suitable primers flanking the SNP markers.

Genetic markers of the present invention include "dominant" or "codominant" markers. "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers.

In addition to SSRs and SNPs, repetitive elements can be used as markers. For most eukaryotes, interspersed repeat sequence elements are typically mobile genetic elements (Wright et al., *Genetics* 142:569-578 (1996), the entirety of which is herein incorporated by reference). They are ubiquitous in most living organisms and are present in copy numbers ranging from just a few elements to tens or hundreds or thousands per genome. In the latter case, they can represent a major fraction of the genome. For example, transposable elements have been estimated to make up greater than 50% of the maize genome (Kidwell, and Lisch *Proc. Natl. Acad. Sci. USA* 94:7704-7711 (1997), the entirety of which is herein incorporated by reference).

Transposable elements are classified in families according to their sequence similarity. Two major classes are distinguished by their differing modes of transposition. Class I elements are retroelements that use reverse transcriptase to transpose by means of an RNA intermediate. They include long terminal repeat retrotransposons and long and short interspersed elements (LINES and SINES, respectively).

Class II elements transpose directly from DNA to DNA and include transposons such as the Activator-Dissociation (Ac-Ds) family in maize, the P element in *Drosophila* and the Tc-1 element in *Caenhorabditis elegans*. Additionally, a category of transposable elements has been discovered whose transposition mechanism is not yet known. These miniature inverted-repeat transposable elements (MITEs) have some properties of both class I and II elements. They are short (100-400 bp in length) and none so far has been found to have any coding potential. They are present in high copy number (3,000-10,000) per genome and have target site preferences for TAA or TA in plants (Kidwell and Lisch, *Proc. Natl. Acad. Sci. USA* 94:7704-7711 (1997)).

Insertion elements are found in two areas of the genome. Some are located in regions distant from gene sequences such as in the heterochromatin or in regions between genes; other repeat elements are found in or near single copy sequences. The insertion of an Ac-Ds element into wx-m9, an allele of the waxy locus in maize is an example of a repetitive element found within a coding region. The effect of this insertion is attenuated by the loss through splicing of the transposable element after transcription (Kidwell and Lisch, *Proc. Natl. Acad. Sci. USA* 94:7704-7711 (1997)).

The genetic variability resulting from transposable elements ranges from changes in the size and arrangement of whole genomes to changes in single nucleotides. They may produce major effects on phenotypic traits or small silent changes detectable only at the DNA sequence level. Transposable elements may also produce variation when they excise, leaving small footprints of their previous presence (Kidwell and Lisch, *Proc. Natl. Acad. Sci. USA* 94:7704-7711 (1997)).

In addition, other markers such as AFLP markers, RFLP markers, RAPD markers, phenotypic markers or isozyme markers can be utilized (Walton, Seed World 22-29, Jul., 1993); Burow and Blake, *Molecular Dissection of Complex Traits*, 13-29, Eds. Paterson, CRC Press, New York (1988), both of which are herein incorporated by reference in their entirety). DNA markers can be developed from nucleic acid molecules using restriction endonucleases, the PCR and/or DNA sequence information. RFLP markers result from single base changes or insertions/deletions. These codominant markers are highly abundant in plant genomes, have a medium level of polymorphism and are developed by a combination of restriction endonuclease digestion and Southern blotting hybridization. CAPS are similarly developed from restriction nuclease digestion but only of specific PCR products. These markers are also codominant, have a medium level of polymorphism and are highly abundant in the genome. The CAPS result from single base changes and insertions/deletions. Another marker type, RAPDs, are developed from DNA amplification with random primers and result from single base changes and insertions/deletions in plant genomes. They are dominant markers with a medium level of polymorphisms and are highly abundant. AFLP markers require using the PCR on a subset of restriction fragments from extended adapter primers. These markers are both dominant and codominant, are highly abundant in genomes and exhibit a medium level of polymorphism. SSRs require DNA sequence information. These codominant markers result from repeat length changes, are highly polymorphic, and do not exhibit as high a degree of abundance in the genome as CAPS, AFLPs and RAPDs. SNPs also require DNA sequence information. These codominant markers result from single base substitutions. They are highly abundant and exhibit a medium of polymorphism (Rafalski et al., In: *Nonmammalian Genomic Analysis*, ed. Birren and Lai, Academic Press, San Diego, Calif., pp. 75-134 (1996), the entirety of which is herein incorporated by reference). Methods to isolate such markers are known in the art.

Long Terminal repeat retrotransposons and MITEs have been found to be associated with the genes of many plants where some of the transposable elements contribute regulatory sequences. MITEs such as the Tourist element in maize and the Stowaway element in Sorghum are found frequently in the 5' and 3' noncoding regions of genes and are frequently associated with the regulatory regions of genes of diverse flowering plants (Kidwell and Lisch, *Proc. Natl. Acad. Sci. USA* 94:7704-7711 (1997)). It is understood that one or more of the Long Terminal repeat retrotransposons and/or MITES may be a marker, and even more preferably a marker for a gene.

(ii) Nucleic Acid Molecules Comprising Regulatory Elements

Another class of agents of the present invention are nucleic acid molecules having promoter regions or partial promoter regions within SEQ ID NO: 1 through SEQ ID NO: 69652 or other nucleic acid molecules of the present invention. Such promoter regions are typically found upstream of the trinucleotide ATG sequence at the start site of a protein coding region.

As used herein, a promoter region is a region of a nucleic acid molecule that is capable, when located in cis to a nucleic acid sequence that encodes for a protein or fragment thereof to function in a way that directs expression of one or more mRNA molecules that encodes for the protein or fragment thereof.

Promoters of the present invention can include between about 300 bp upstream and about 10 kb upstream of the trinucleotide ATG sequence at the start site of a protein coding region. Promoters of the present invention can preferably include between about 300 bp upstream and about 5 kb upstream of the trinucleotide ATG sequence at the start site of a protein coding region. Promoters of the present invention can more preferably include between about 300 bp up-stream and about 2 kb upstream of the trinucleotide ATG sequence at the start site of a protein coding region. Promoters of the present invention can include between about 300 bp upstream and about 1 kb upstream of the trinucleotide ATG sequence at the start site of a protein coding region. While in many circumstances a 300 bp promoter may be sufficient for expression, additional sequences may act to further regulate expression, for example, in response to biochemical, developmental or environmental signals.

It is also preferred that the promoters of the present invention contain a CAAT and a TATA cis element. Moreover, the promoters of the present invention can contain one or more cis elements in addition to a CAAT and a TATA box.

By "regulatory element" it is intended a series of nucleotides that determines if, when, and at what level a particular gene is expressed. The regulatory DNA sequences specifically interact with regulatory or other proteins. Many regulatory elements act in cis ("cis elements") and are believed to affect DNA topology, producing local conformations that selectively allow or restrict access of RNA polymerase to the DNA template or that facilitate selective opening of the double helix at the site of transcriptional initiation. Cis elements occur within, but are not limited to promoters, and promoter modulating sequences (inducible elements). Cis elements can be identified using known cis elements as a target sequence or target motif in the BLAST programs of the present invention.

Promoters of the present invention include homologues of cis elements known to effect gene regulation that show homology with the nucleic acid molecules of the present invention. These cis elements include, but are not limited to, oxygen responsive cis elements (Cowen et al., *J Biol. Chem.* 268(36):26904-26910 (1993) the entirety of which is herein incorporated by reference), light regulatory elements (Bruce et al., *Plant Cell* 2 (11):1081-1089 (1990); Bruce et al., *EMBO J.* 10:3015-3024 (1991); Rocholl et al., *Plant Sci.* 97:189-198 (1994); Block et al., *Proc. Natl. Acad. Sci. USA* 87:5387-5391 (1990); Giuliano et al., *Proc. Natl. Acad. Sci. USA* 85:7089-7093 (1988); Staiger et al., *Proc. Natl. Acad. Sci. USA* 86:6930-6934 (1989); Izawa et al., *Plant Cell* 6:1277-1287 (1994); Menkens et al., *Trends in Biochemistry* 20:506-510 (1995); Foster et al., *FASEB J.* 8:192-200 (1994); Plesse et al., *Mol Gen Gene* 254:258-266 (1997); Green et al., *EMBO J.* 6:2543-2549 (1987); Kuhlemeier et al., *Ann. Rev Plant Physiol.* 38:221-257 (1987); Villain et al., *J. Biol. Chem.* 271:32593-32598 (1996); Lam et al., *Plant Cell* 2:857-866 (1990); Gilmartin et al., *Plant Cell* 2:369-378 (1990); Datta et al., *Plant Cell* 1:1069-1077 (1989); Castresana et al., *EMBO J.* 7:1929-1936 (1988); Ueda et al., *Plant Cell* 1:217-227 (1989); Terzaghi et al., *Annu. Rev. Plant Physiol. Plant Mol. Biol.* 46:445-474 (1995); Tjaden et al., *Plant Cell* 6:107-118 (1994); Tjaden et al., *Plant Physiol.* 108:1109-1117 (1995); Ngai et al., *Plant J.* 12:1021-1234 (1997), all of which are herein incorporated by reference in their entirety), elements responsive to gibberellin, (Muller et al., *J. Plant Physiol.* 145:606-613 (1995); Croissant et al., *Plant Science* 116:27-35 (1996); Lohmer et al., *EMBO J.* 10:617-624 (1991); Rogers et al., *Plant Cell* 4:1443-1451 (1992); Lanahan et al., *Plant Cell* 4:203-211 (1992); Skriver et al., *Proc. Natl. Acad. Sci. USA* 88:7266-7270 (1991); Gilmartin et al., *Plant Cell* 2:369-378 (1990); Huang et al., *Plant Mol. Biol.* 14:655-668 (1990); Gubler et al., *Plant Cell* 7:1879-1891 (1995), all of which are herein incorporated by reference in their entirety), elements responsive to abscisic acid, (Busk et al., *Plant Cell* 9:2261-2270 (1997); Guiltinan et al., *Science* 250:267-270 (1990); Shen et al., *Plant Cell* 7:295-307 (1995); Shen et al., *Plant Cell* 8:1107-1119 (1996); Seo et al., *Plant Mol. Biol.* 27:1119-1131 (1995); Marcotte et al., *Plant Cell* 1:969-976 (1989); Shen et al., *Plant Cell* 7:295-307 (1995); Iwasaki et al., *Mol Gen Genet* 247:391-398 (1995); Hattori et al., *Genes Dev.* 6:609-618 (1992); Thomas et al., *Plant Cell* 5:1401-1410 (1993), all of which are herein incorporated by reference in their entirety), elements similar to abscisic acid responsive elements, (Ellerstrom et al., *Plant Mol. Biol.* 32:1019-1027 (1996), the entirety of which is herein incorporated by reference), auxin responsive elements (Liu et al., *Plant Cell* 6:645-657 (1994); Liu et al., *Plant Physiol.* 115:397-407 (1997); Kosugi et al., *Plant J.* 7:877-886 (1995); Kosugi et al., *Plant Cell* 9:1607-1619 (1997); Ballas et al., *J. Mol. Biol.* 233:580-596 (1993), all of which are herein incorporated by reference in their entirety), a cis element responsive to methyl jasmonate treatment (Beaudoin and Rothstein, *Plant Mol. Biol.* 33:835-846 (1997), the entirety of which is herein incorporated by reference), a cis element responsive to abscisic acid and stress response (Straub et al., *Plant Mol. Biol.* 26:617-630 (1994), the entirety of which is herein incorporated by reference), ethylene responsive cis elements (Itzhaki et al., *Proc. Natl. Acad. Sci. USA* 91:8925-8929 (1994); Montgomery et al., *Proc. Natl. Acad. Sci. USA* 90:5939-5943 (1993); Sessa et al., *Plant Mol. Biol.* 28:145-153 (1995); Shinshi et al., *Plant Mol. Biol.* 27:923-932 (1995), all of which are herein incorporated by reference in their entirety), salicylic acid cis responsive elements, (Strange et al., *Plant J.* 11:1315-1324 (1997); Qin et al., *Plant Cell* 6:863-874 (1994), both of which are herein incorporated by reference in their entirety), a cis element that responds to water stress and abscisic acid (Lam et al., *J. Biol. Chem.* 266:17131-17135 (1991); Thomas et al., *Plant Cell* 5:1401-1410 (1993); Pla et al., *Plant Mol Biol* 21:259-266 (1993), all of which are herein incorporated by reference in their entirety), a cis element essential for M phase-specific expression (Ito et al., *Plant Cell* 10:331-341 (1998), the entirety of which is herein incorporated by reference), sucrose responsive elements (Huang et al., *Plant Mol. Biol.* 14:655-668 (1990); Hwang et al., *Plant Mol Biol* 36:331-341 (1998); Grierson et al., *Plant J.* 5:815-826 (1994), all of which are herein incorporated by reference in their entirety), heat shock response elements (Pelham et al., *Trends Genet.* 1:31-35 (1985), the entirety of which is herein incorporated by reference), elements responsive to auxin and/or salicylic acid and also reported for light regulation (Lam et al., *Proc. Natl. Acad. Sci. USA* 86:7890-7897 (1989); Benfey et al., *Science* 250:959-966 (1990), both of which are herein incorporated by reference in their entirety), elements responsive to ethylene and salicylic acid (Ohme-Takagi et al., *Plant Mol. Biol.* 15:941-946 (1990), the entirety of which is herein incorporated by reference), elements responsive to wounding and abiotic stress (Loake et al., *Proc. Natl. Acad. Sci. USA* 89:9230-9234 (1992); Mhiri et al., *Plant Mol. Biol.* 33:257-266 (1997), both of which are herein incorporated by reference in their entirety), antioxidant response elements (Rushmore et al., *J. Biol. Chem.* 266:11632-11639; Dalton et al., *Nucleic Acids Res.* 22:5016-5023 (1994), both of which are herein incorporated by reference in their entirety), Sph elements (Suzuki et al., *Plant Cell* 9:799-807 1997), the entirety of which is herein incorporated reference), Elicitor responsive elements, (Fukuda et al., *Plant Mol. Biol.* 34:81-87 (1997); Rushton et al., *EMBO J.* 15:5690-5700 (1996), both of which are herein incorporated by reference in their entirety), metal responsive elements (Stuart et al., *Nature* 317:828-831 (1985); Westin et al., *EMBO J.* 7:3763-3770 (1988); Thiele et al., *Nucleic Acids Res.* 20:1183-1191 (1992); Faisst et al., *Nucleic Acids Res.* 20:3-26 (1992), all of which are herein incorporated by reference in their entirety), low temperature responsive elements, (Baker et al., *Plant Mol. Biol.* 24:701-713 (1994); Jiang et al., *Plant Mol. Biol.* 30:679-684 (1996); Nordin et al., *Plant Mol. Biol.* 21:641-653 (1993); Zhou et al., *J. Biol. Chem.* 267:23515-23519 (1992), all of which are herein incorporated by reference in their entirety), drought responsive elements, (Yamaguchi et al., *Plant Cell* 6:251-264 (1994); Wang et al., *Plant Mol. Biol.* 28:605-617 (1995); Bray E A, *Trends in Plant Science* 2:48-54 (1997), all of which are herein incorporated by reference in their entirety); enhancer elements for glutenin, (Colot et al., *EMBO J.* 6:3559-3564 (1987); Thomas et al., *Plant Cell* 2:1171-1180 (1990); Kreis et al., *Philos. Trans. R. Soc. Lond., B* 314:355-365 (1986), all of which are herein incorporated by reference in their entirety), light-independent regulatory elements, (Lagrange et al., *Plant Cell* 9:1469-1479 (1997); Villain et al., *J. Biol. Chem.* 271:32593-32598 (1996), both of which are herein incorporated by reference in their entirety), OCS enhancer elements, (Bouchez et al., *EMBO J.* 8:4197-4204 (1989); Foley et al., *Plant J.* 3:669-679 (1993), both of which are herein incorporated by reference in their entirety), ACGT elements, (Foster et al., *FASEB J.* 8:192-200 (1994); Izawa et al., *Plant Cell* 6:1277-1287 (1994); Izawa et al., *J. Mol. Biol.* 230:1131-1144 (1993), all of which are herein incorporated by reference in their entirety), negative cis elements in plastid related genes, (Zhou et al., *J. Biol. Chem.* 267:23515-23519 (1992); Lagrange et al., *Mol. Cell Biol.* 13:2614-2622 (1993); Lagrange et al., *Plant Cell* 9:1469-1479 (1997); Zhou et al., *J. Biol. Chem.* 267:23515-23519 (1992), all of which are herein incorporated by reference in their entirety), prolamin box elements, (Forde et al., *Nucleic Acids Res.* 13:7327-7339 (1985); Colot et al., *EMBO J.* 6:3559-3564 (1987); Thomas et al., *Plant Cell* 2:1171-1180 (1990); Thompson et al., *Plant Mol. Biol.* 15:755-764 (1990); Vicente et al., *Proc. Natl. Acad. Sci. USA* 94:7685-7690 (1997), all of which are herein incorporated by reference in their entirety), elements in enhancers from the IgM heavy chain gene (Gillies et al., *Cell* 33:717-728 (1983); Whittier et al., *Nucleic Acids Res.* 15:2515-2535 (1987), both of which are herein incorporated by reference in their entirety).

(iii) Nucleic Acid Molecules Comprising Genes or Fragments Thereof

Nucleic acid molecules of the present invention can comprise one or more genes or fragments thereof. Such genes or fragments thereof include homologues of known genes or protein coding regions in other organisms or genes or fragments thereof that elicit only limited or no matches with known genes or protein coding regions.

Genomic sequences can be screened for the presence of protein homologues or genes utilizing one or a number of different search algorithms have that been developed, one example of which are the suite of programs referred to as BLAST programs. Other examples of suitable programs that can be utilized are known in the art, several of which are described above in the Background and under the section titled "Uses of the Agents of the Invention." In addition, unidentified reading frames may be screened for protein coding regions by prediction software such as GenScan, which is located at the website gnomic.standford.edu/GENSCAN-W.html.

In a preferred embodiment of the present invention, the rice protein or fragment thereof of the present invention is a homologue of another plant protein. In another preferred embodiment of the present invention, the rice protein or fragment thereof is a homologue of a plant protein. In another preferred embodiment of the present invention, the rice protein or fragment thereof of the present invention is a homologue of a cereal protein. In another preferred embodiment of the present invention, the rice protein or fragment thereof of the present invention is a homologue of a fungal protein. In another preferred embodiment of the present invention, the rice protein or fragment thereof of the present invention is a homologue of a mammalian protein. In another preferred embodiment of the present invention, the rice protein or fragment thereof of the present invention is a homologue of a bacterial protein. In another preferred embodiment of the present invention, the rice protein or fragment thereof of the present invention is a homologue of an algal protein.

In a preferred embodiment of the present invention, the rice protein or fragments thereof or nucleic acid molecule or fragment thereof has a BLAST score of more than 200, preferably a BLAST score of more than 300, even more preferably a BLAST score of more than 400 with its homologue.

In another preferred embodiment of the present invention, the nucleic acid molecule encoding the rice protein or fragment thereof and/or nucleic acid molecule or fragment thereof exhibits a % identity with its homologue of between about 25% and about 40%, more preferably of between about 40 and about 70%, even more preferably of between about 70% and about 90%, and even more preferably between about 90% and 99%. In another preferred embodiment, of the present invention, the nucleic acid molecule encoding the rice protein or fragment thereof exhibits a % identity with its homologue of 100%.

In a preferred embodiment of the present invention, the rice protein or fragment thereof or nucleic acid molecule or fragment thereof exhibits a % coverage of between about 0% and about 33%, more preferably of between about 34% and about 66%, and even more preferably of between about 67% and about 100%.

Genomic sequences can be screened for the presence of proteins utilizing one or a number of different search algorithms have that been developed, one example of which are the suite of programs referred to as BLAST programs. Other examples of suitable programs that can be utilized are known in the art, several of which are described above in the Background. Nucleic acid molecules of the present invention also include non-rice homologues. Preferred non-rice homologues are selected from the group consisting of alfalfa, *Arabidopsis* barley, *Brassica*, broccoli, cabbage, citrus, cotton, garlic, oat, oilseed rape, onion, canola, flax, an ornamental plant, maize, pea, peanut, pepper, potato, rye, sorghum, soybean, strawberry, sugarcane, sugarbeet, tomato, wheat, poplar, pine, fir, eucalyptus, apple, lettuce, lentils, grape, banana, tea, turf grasses, sunflower, oil palm, and *Phaseolus*.

In a preferred embodiment, nucleic acid molecules having SEQ ID NO: 1 through SEQ ID NO: 69652 or complements and fragments of either or other nucleic acid molecules of the present invention can be utilized to obtain such homologues.

The degeneracy of the genetic code, which allows different nucleic acid sequences to code for the same protein or peptide, is known in the literature. (U.S. Pat. No. 4,757,006, the entirety of which is herein incorporated by reference). As used herein a nucleic acid molecule is degenerate of another nucleic acid molecule when the nucleic acid molecules encode for the same amino acid sequences but comprise different nucleotide sequences. An aspect of the present invention is that the nucleic acid molecules of the present invention include nucleic acid molecules that are degenerate of those set forth in SEQ ID NO: 1 through to SEQ ID NO: 69652 or complements thereof.

In a further aspect of the present invention, one or more of the nucleic acid molecules of the present invention differ in nucleic acid sequence from those encoding a rice protein or fragment thereof in SEQ ID NO: 1 through SEQ ID NO: 69652 or complements thereof due to the degeneracy in the genetic code in that they encode the same protein but differ in nucleic acid sequence. In another further aspect of the present invention, one or more of the nucleic acid molecules of the present invention differ in nucleic acid sequence from those encoding a rice homologue or fragment thereof in SEQ ID NO: 1 through SEQ ID NO: 69652 or complements thereof due to the fact that the different nucleic acid sequence encodes a protein having one or more conservative amino acid residues. In such amino acid sequences, one or more amino acids in the fundamental sequence are substituted with another amino acid(s), the charge and polarity of which are similar to that of the native amino acid, i.e., a conservative amino acid substitution, resulting in a silent change.

Substitutes for an amino acid within the fundamental polypeptide sequence can be selected from other members of the class to which the naturally occurring amino acid belongs. Amino acids can be divided into the following four groups: (1) acidic amino acids, (2) basic amino acids, (3) neutral polar amino acids, and (4) neutral nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid changes within the fundamental polypeptides sequence can be made by substituting one amino acid within one of these groups with another amino acid within the same group.

It is also understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, obtain a protein with like properties.

In making such changes, the hydropathic index of amino acids may be considered. The importance of the hydropathic amino acid index in conferring interactive biological function on a protein is generally understood in the art (Kyte and Doolittle, *J. Mol. Biol.* 157, 105-132 (1982), herein incorporated by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.* 157, 105-132 (1982); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

It is known in the art that certain amino acid may be substituted by other amino acids having a similar hydropathic index or score and still result in a protein with similar biological activities, i.e., still obtain a biologically functional equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference in its entirety, states that the greatest local average hydrophilicity of a protein, as govern by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

It is known in the art that certain amino acid may be substituted by other amino acids having a similar hydrophilicity value and still result in a protein with similar biological activities, i.e., still obtain a biologically functional equivalent protein. In making such changes, the substitution of amino acids whose hydrophilicity values are within ±2 is preferred, those which are within ±1 are particularly preferred, and those within ±0.5 are even more particularly preferred.

(iv) Nucleic Acid Molecules Comprising Introns and/or Intron/Exon Junctions

Nucleic acid molecules of the present invention can comprise an intron and/or one or more intron/exon junction. Sequences of the present invention can be screened for introns and intron/exon junctions utilizing one or a number of different search algorithms that have that been developed, one example of which are the suite of programs referred to as BLAST programs. Other examples of suitable programs that can be utilized are known in the art, several of which are described above in the Background and in the section entitled "Uses of the Agents of the Present Invention."

(b) Protein and Peptide Molecules

A class of agents includes one or more of the protein or peptide molecules, including those encoded by nucleic acid molecules disclosed in Table 1 of U.S. application Ser. No. 09/620,392 filed Jul. 19, 2000 (the entirety of which is incorporated by reference herein), fragments thereof or complements thereof or one or more of the proteins encoded by a nucleic acid molecule or fragment thereof or peptide molecules encoded by other nucleic acid agents of the present invention. Protein and peptide molecules can be identified using known protein or peptide molecules as a target sequence or target motif in the BLAST programs of the present invention. In a preferred embodiment, the protein or peptide molecules of the present invention are derived from rice and more preferably *Oryza sativa* L (japonica type), more preferably *Oryza sativa* L (japonica type), cv. Nipponbare.

As used herein, the term "protein molecule" or "peptide molecule" includes any molecule that comprises five or more amino acids. It is well known in the art that proteins or peptides may undergo modification, including post-translational modifications, such as, but not limited to, disulfide bond formation, glycosylation, phosphorylation, or oligomerization. Thus, as used herein, the term "protein molecule" or "peptide molecule" includes any protein molecule that is modified by any biological or non-biological process. The terms "amino acid" and "amino acids" refer to all naturally occurring L-amino acids. This definition is meant to include norleucine, ornithine, homocysteine, and homoserine.

One or more of the protein or fragments of peptide molecules may be produced via chemical synthesis, or more preferably, by expression in a suitable bacterial or eukaryotic host. Suitable methods for expression are described by Sambrook et al., *Molecular Cloning, A Laboratory Manual*, 2nd Edition, Cold Spring Harbor Press, Cold Spring Harbor, N.Y. (1989), or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin, etc.). Fusion protein or peptide molecules of the present invention are preferably produced via recombinant means.

Another class of agents comprises protein or peptide molecules encoded by SEQ ID NO: 1 through SEQ ID NO: 69652 or complements thereof or, fragments or fusions thereof in which conservative, non-essential, or not relevant, amino acid residues have been added, replaced, or deleted. An example of such a homologue is the homologue protein of all non-rice plant species, including but not limited to alfalfa, barley, *Brassica*, broccoli, cabbage, citrus, cotton, garlic, oat, oilseed rape, onion, canola, flax, an ornamental plant, pea, peanut, pepper, potato, maize, rye, sorghum, soybean, strawberry, sugarcane, sugarbeet, tomato, wheat, poplar, pine, fir, eucalyptus, apple, lettuce, peas, lentils, grape, banana, wheat, tea, turf grasses, etc. Particularly preferred non-rice plants to utilize for the isolation of homologues would include alfalfa, barley, cotton, oat, oilseed rape, maize, canola, ornamentals, sugarcane, sugarbeet, tomato, potato, wheat, and turf grasses. Such a homologue can be obtained by any of a variety of methods. Most preferably, as indicated above, one or more of the disclosed sequences (SEQ ID NO: 1 through SEQ ID NO: 69652 or complements thereof) will be used to define a pair of primers that may be used to isolate the homologue-encoding nucleic acid molecules from any desired species. Such molecules can be expressed to yield homologues by recombinant means. A homologue can also be generated by molecular evolution or DNA shuffling techniques, so that the molecule retains at least one function or structure characteristic of the original protein (see, for example, U.S. Pat. No. 5,811,238).

(c) Antibodies

One aspect of the present invention concerns antibodies, single-chain antigen binding molecules, or other proteins that specifically bind to one or more of the protein or peptide molecules of the present invention and their homologues, fusions or fragments. Such antibodies may be used to quantitatively or qualitatively detect the protein or peptide molecules of the present invention. As used herein, an antibody or peptide is said to "specifically bind" to a protein or peptide molecule of the present invention if such binding is not competitively inhibited by the presence of non-related molecules. In a preferred embodiment the antibodies of the present invention bind to proteins derived from rice and more preferably bind to proteins or fragments thereof of rice In a preferred embodiment the nucleic acid molecules of the present invention are derived from rice and more preferably *Oryza sativa* L (japonica type), more preferably *Oryza sativa* L (japonica type), cv. Nipponbare.

Nucleic acid molecules that encode all or part of the protein of the present invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind proteins and protein fragments of the present invention may be polyclonal or monoclonal, and may comprise intact immunoglobulins, or antigen binding portions of immunoglobulins (such as (F(ab'), F(ab')₂ fragments), or single-chain immunoglobulins producible, for example, via recombinant means). It is understood that practitioners are familiar with the standard resource materials which describe specific conditions and procedures for the construction, manipulation and isolation of antibodies (see, for example, Harlow and Lane, *Antibodies: A Laboratory Manual*, Cold Spring Harbor Press, Cold Spring Harbor, N.Y. (1988), the entirety of which is herein incorporated by reference).

Murine monoclonal antibodies are particularly preferred. BALB/c mice are preferred for this purpose, however, equivalent strains may also be used. The animals are preferably immunized with approximately 25 μg of purified protein (or fragment thereof) that has been emulsified in a suitable adjuvant (such as TiterMax adjuvant (Vaxcel, Norcross, Ga.)). Immunization is preferably conducted at two intramuscular sites, one intraperitoneal site, and one subcutaneous site at the base of the tail. An additional i.v. injection of approximately 25 μg of antigen is preferably given in normal saline three weeks later. After approximately 11 days following the second injection, the mice may be bled and the blood screened for the presence of anti-protein or peptide antibodies. Preferably, a direct binding Enzyme-Linked Immunoassay (ELISA) is employed for this purpose.

More preferably, the mouse having the highest antibody titer is given a third i.v. injection of approximately 25 μg of the same protein or fragment. The splenic leukocytes from this animal may be recovered 3 days later, and are then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting clones may then be screened for their capacity to produce monoclonal antibodies ("mAbs"), preferably by direct ELISA.

In one embodiment, anti-protein or peptide monoclonal antibodies are isolated using a fusion of a protein, protein fragment, or peptide of the present invention, or conjugate of a protein, protein fragment, or peptide of the present invention, as immunogens. Thus, for example, a group of mice can be immunized using a fusion protein emulsified in Freund's complete adjuvant (e.g., approximately 50 μg of antigen per immunization). At three week intervals, an identical amount of antigen is emulsified in Freund's incomplete adjuvant and used to immunize the animals. Ten days following the third immunization, serum samples are taken and evaluated for the presence of antibody. If antibody titers are too low, a fourth booster can be employed. Polysera capable of binding the protein or peptide can also be obtained using this method.

In a preferred procedure for obtaining monoclonal antibodies, the spleens of the above-described immunized mice are removed, disrupted, and immune splenocytes are isolated over a ficoll gradient. The isolated splenocytes are fused, using polyethylene glycol with BALB/c-derived HGPRT (hypoxanthine guanine phosphoribosyl transferase) deficient P3x63xAg8.653 plasmacytoma cells. The fused cells are plated into 96-well microtiter plates and screened for hybridoma fusion cells by their capacity to grow in culture medium supplemented with hypothanthine, aminopterin and thymidine for approximately 2-3 weeks.

Hybridoma cells that arise from such incubation are preferably screened for their capacity to produce an immunoglobulin that binds to a protein of interest. An indirect ELISA may be used for this purpose. In brief, the supernatants of hybridomas are incubated in microtiter wells that contain immobilized protein. After washing, the titer of bound immunoglobulin can be determined using, for example, a goat anti-mouse antibody conjugated to horseradish peroxidase. After additional washing, the amount of immobilized enzyme is determined (for example through the use of a chromogenic substrate). Such screening is performed as quickly as possible after the identification of the hybridoma in order to ensure that a desired clone is not overgrown by non-secreting neighbors. Desirably, the fusion plates are screened several times since the rates of hybridoma growth vary. In a preferred sub-embodiment, a different antigenic form of immunogen may be used to screen the hybridoma. Thus, for example, the splenocytes may be immunized with one immunogen, but the resulting hybridomas can be screened using a different immunogen. It is understood that any of the protein or peptide molecules of the present invention may be used to raise antibodies.

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the present invention permits the identification of mimetic compounds of those molecules. A "mimetic compound" is a compound that is not that compound, or a fragment of that compound, but which nonetheless exhibits an ability to specifically bind to antibodies directed against that compound.

It is understood that any of the agents of the present invention can be substantially purified and/or be biologically active and/or recombinant.

Exemplary Uses of the Agents of the Invention

Nucleic acid molecules and fragments thereof of the present invention may be employed for genetic mapping studies using linkage analysis (genetic markers). A genetic linkage map shows the relative locations of specific DNA markers along a chromosome. Maps are used for the identification of genes associated with genetic diseases or phenotypic traits, comparative genomics, and as a guide for physical mapping. Through genetic mapping, a fine scale linkage map can be developed using DNA markers, and, then, a genomic DNA library of large-sized fragments can be screened with molecular markers linked to the desired trait. In a preferred embodiment of the present invention, the genomic library screened with the nucleic acid molecules of the present invention is a genomic library of rice.

Mapping marker locations is based on the observation that two markers located near each other on the same chromosome will tend to be passed together from parent to offspring. During gamete production, DNA strands occasionally break and rejoin in different places on the same chromosome or on the homologous chromosome. The closer the markers are to each other, the more tightly linked and the less likely a recombination event will fall between and separate them. Recombination frequency thus provides an estimate of the distance between two markers.

In segregating populations, target genes have been reported to have been placed within an interval of 5-10 cM with a high degree of certainty (Tanksley et al., *Trends in Genetics* 11(2): 63-68 (1995), the entirety of which is herein incorporated by reference). The markers defining this interval are used to screen a larger segregating population to identify individuals derived from one or more gametes containing a crossover in the given interval. Such individuals are useful in orienting other markers closer to the target gene. Once identified, these individuals can be analyzed in relation to all molecular markers within the region to identify those closest to the target.

Markers of the present invention can be employed to construct linkage maps and to locate genes with qualitative and quantitative effects. The genetic linkage of additional marker molecules can be established by a genetic mapping model such as, without limitation, the flanking marker model reported by Lander and Botstein, *Genetics*, 121:185-199 (1989), and the interval mapping, based on maximum likelihood methods described by Lander and Botstein, *Genetics*, 121:185-199 (1989), the entirety of which is herein incorporated by reference and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990)). Additional software includes Qgene, Version 2.23 (1996), Department of Plant Breeding and Biometry, 266 Emerson Hall, Cornell University, Ithaca, N.Y., the manual of which is herein incorporated by reference in its entirety). Use of the Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics*, 121:185-199 (1989), the entirety of which is herein incorporated by reference and further described by Arús and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak and Lander, *Genetics*, 139:1421-1428 (1995), the entirety of which is herein incorporated by reference). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994). Procedures combining interval mapping with regression analysis, whereby the phenotype is regressed onto a single putative QTL at a given marker interval, and at the same time onto a number of markers that serve as 'cofactors,' have been reported by Jansen and Stam, *Genetics*, 136:1447-1455 (1994) and Zeng, *Genetics*, 136:1457-1468 (1994). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng, *Genetics*, 136:1457-1468 (1994). These models can be extended to multi-environment experiments to analysis genotype-environment interactions (Jansen et al., *Theo. Appl. Genet.* 91:33-37 (1995).

Selection of an appropriate mapping population is important to map construction. The choice of appropriate mapping population depends on the type of marker systems employed (Tanksley et al., J. P. *Gustafson and R. Appels* (eds.), Plenum Press, New York, pp. 157-173 (1988), the entirety of which is herein incorporated by reference). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

An $F_2$ population is the first generation of selfing after the hybrid seed is produced. Usually a single $F_1$ plant is selfed to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938), the entirety of which is herein incorporated by reference). In the case of dominant markers, progeny tests (e.g., $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g., disease resistance) or where trait expression is controlled by a QTL. Segregation data from progeny test populations (e.g., $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually $>F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter, *Proc. Natl. Acad. Sci. USA* 89:1477-1481 (1992)). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci. USA* 89:1477-1481 (1992)). Information obtained from backcross populations using either codominant or dominant makers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e., about 0.15% recombination). Increased recombination can be beneficial for resolution of tight linkages, but may be undesirable in the construction of maps with low marker saturation.

Near-isogenic lines (NIL)(created by many backcrosses to produce an array of individuals that are nearly identical in genetic composition except for the trait or genomic region under interrogation) can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al., *Proc. Natl. Acad. Sci. USA* 88:9828-9832 (1991)). In BSA, two bulked DNA samples are drawn from a segregating population originating from a single cross. These bulks contain individuals that are identical for a particular trait (resistant or susceptible to particular disease) or genomic region but arbitrary at unlinked regions (i.e., heterozygous). Regions unlinked to the target region will not differ between the bulked samples of many individuals in BSA.

It is understood that one or more of the nucleic acid molecules of the present invention may in one embodiment be used as markers in genetic mapping. In a preferred embodiment, nucleic acid molecules of the present invention may in one embodiment be used as markers with rice.

The nucleic acid molecules of the present invention may be used for physical mapping. Physical mapping, in conjunction with linkage analysis, can enable the isolation of genes. Physical mapping has been reported to identify the markers closest in terms of genetic recombination to a gene target for cloning. Once a DNA marker is linked to a gene of interest, the chromosome walking technique can be used to find the genes via overlapping clones. For chromosome walking, random molecular markers or established molecular linkage maps are used to conduct a search to localize the gene adjacent to one or more markers. A chromosome walk (Bukanov et al., *Mol. Microbiol,* 11:509-523 (1994); Birkenbihl et al., *Nucleic Acids Res.* 17:5057-5069 (1989); Wenzel et al., *Nucleic Acids Res.* 16:8323-8336, (1988), all of which are herein incorporated by reference in their entirety) is then initiated from the closest linked marker. Starting from the selected clones, labeled probes specific for the ends of the insert DNA are synthesized and used as probes in hybridizations against a representative library. Clones hybridizing with one of the probes are picked and serve as templates for the synthesis of new probes; by subsequent analysis, contigs are produced.

The degree of overlap of the hybridizing clones used to produce a contig can be determined by comparative restriction analysis. Comparative restriction analysis can be carried out in different ways all of which exploit the same principle; two clones of a library are very likely to overlap if they contain a limited number of restriction sites for one or more restriction endonucleases located at the same distance from each other. The most frequently used procedures are, finger-printing (Coulson et al., *Proc. Natl. Acad. Sci. USA* 83:7821-7821, (1986); Knott et al., *Nucleic Acids Res.* 16:2601-2612 (1988); Eiglmeier et al., *Mol. Microbiol.* 7(2): 197-206 (1993), all of which are herein incorporated by reference in their entirety), restriction fragment mapping (Smith and Birnstiel, *Nucleic Acids Res.* 3:2387-2398 (1976), the entirety of which is herein incorporated by reference), or the "landmarking" technique (Charlebois et al., *J. Mol. Biol.* 222:509-524 (1991), the entirety of which is herein incorporated by reference).

To generate a physical map of a genome with BACs using the fingerprinting technique, a BAC library containing a number of clones equivalent to 4×-20× haploid genome can be used. (Zhang and Wing, *Plant Mol. Bio.* 35:115-127 (1997)). For example, BAC DNA can be purified with the conventional alkaline lysis procedure as used for plasmid DNA purification, digested with the restriction enzyme used for construction of the BAC libraries and end-labeled with $^{32}$P-dATP, digested with Sau3AI and fractionated on a denaturing polyacrylamide gel. The gel is dried to chromatography paper and exposed to X-ray film. Fingerprints are scanned and then converted into database records, according to the positions of each band relative to the bands of the closest molecular-weight marker on a gel. The incoming database of finger-prints are first compared against each other to assemble contigs if overlapped, and then compared against all existing databases to place the incoming BACs and BAC contigs in established contigs if overlapped. The physical length of a contig in kb is estimated according to the number of restriction sites of the enzyme used for the first digestion prior to fragment end labeling.

Restriction analysis of a certain clone can be carried out, for example, according to a method originally described by Smith and Berstiel, *Nucleic Acids Res.* 3:2387-2398 (1976). First, the number and size of cloned restriction fragments to be mapped are determined by complete digestion and agarose gel electrophoresis. Then, the clone is linearized at a unique restriction site outside of the cloned DNA. Aliquots of the linearized molecules are digested to different extents with the enzyme selected for mapping. These partially cut samples are separated on agarose gels, blotted, and hybridized to a labeled fragment of vector DNA. This probe is derived entirely from one side or the other of the unique site used to linearize the clone.

The results show a ladder of DNA fragments that have the same unique end. By repeating these analyses in pairs with all the neighboring intermediate DNA fragments, the correct order of restriction fragments as well as the orientation of the cloned insert can be deduced. The order of restriction fragments produced by restriction enzymes other than the cloning enzyme can be determined similarly. Fragment data from different enzymes are then combined by a computer program and compared with the alignments of other clones of the library (Kohara et al., *Cell* 50:495-508 (1987), the entirety of which is herein incorporated by reference).

The landmarking technique can be carried out without any labeling and relies on agarose gel analysis. Clones are first digested preferably with a 6 bp specific endonuclease A, if possible with the original clone enzyme. Clones are then digested with a second endonuclease B. Endonuclease B is chosen based on its ability to cut rarely in the genome, for example, on average only once in 30 kbp. Of the fragments generated by digestion of one clone with enzyme A, statistically only a small number (between zero and three fragments) will also be cut by enzyme B. The very specific pattern of those fragments which are produced by double digestion are easily recognized. Any of these fragments which have a restriction site for the rarely cutting endonuclease is called a "landmark" Generally one common landmark is sufficient for defining two overlapping clones.

Alternatively to chromosome walking and the associated comparative restriction analyses methods, chromosome landing also has been reported to be used to locate a gene of interest (Tanksley et al., *Trends in Genetics* 11(2):63-68 (1995), the entirety of which is herein incorporated by reference). For chromosome landing, a DNA marker is isolated at a physical distance from the targeted gene. High resolution linkage analysis is used to identify such a marker that cosegregates with the gene. The marker is isolated at a distance that is less than the average insert size of the genomic library used for clone isolation. The DNA marker is then used to screen the library and isolate (or "land" on) the clone containing the gene without chromosome walking. Genome coverage of a library can also be determined by cross-hybridization of individual large insert clones by screening a BAC library with single copy RFLP markers distributed randomly across the genome by hybridization. To assure accuracy of the physical map, the markers should be single-copy or of single-locus origin, if multiple-copy.

Chromosome landing of large-insert clones using chromosome-specific DNA markers such as STSs microsatellites, RFLPs, or other markers can correlate physical and genetic maps (Zwick et al., *Genetics* 148:1983-1992 (1998), the entirety of which is herein incorporated by reference). These strategies include chromosome landing of BACs containing markers or BAC contigs by BAC-FISH (Fluorescent In Situ Hybridization), a technique that involves tagging the DNA marker with an observable label. BAC clones giving positive hybridization signals are individually analyzed by FISH to metaphase chromosome spreads. The location of the labeled probe can be detected after it binds to its complementary DNA strand in an intact chromosome. The FISH of a BAC selected from a BAC contig will directly place the BAC contig to a specific chromosome region and establish a linkage relationships of the BAC contig to another BAC contig.

Markers have been used in physical mapping studies with BAC libraries made from plant genomes. Such mapping studies have been carried out in rice (Kim et al., *Genomics* 34:213-218 (1996); Hang, *Plant Mol. Biol.* 35:129-133 (1997); Zhang and Wing, *Plant Mol. Bio.* 35:115-127 (1997); Chen et al., *Proc. Natl. Acad. Sci. USA* 94:3431-3435 (1997); Wang et al., *Plant J.* 7:525-533 (1995), all of which are herein incorporated by reference in their entirety), sorghum (Zwick et al., *Genetics* 148:1983-1992 (1998); Zhang, et al., *Molecular Breeding* 2:11-24 (1996), both of which are herein incorporated by reference in their entirety) maize, (Chen, et al., *Proc. Natl. Acad. Sci. USA* 94:3431-3435 (1997)), and *Arabidopsis* (Kim, et al., *Genomics* 34:213-218 (1996), the entirety of which is herein incorporated by reference).

Repetitive elements have been used in physical mapping in cereals (Ananiev, et al., *Proc. Natl. Acad. Sci. USA* 95:13073-8 (1998); McLean et al., *Mol Gen Genet* 253:687-694 (1997), both of which are herein incorporated by reference in their entirety).

It is understood that the nucleic acid molecules of the present invention may in one embodiment be used in physical mapping. In a preferred embodiment, nucleic acid molecules of the present invention may in one embodiment be used in the physical mapping of rice.

Nucleic acid molecules of the present invention can be used in comparative mapping (physical and genetic) and to isolate molecules from other cereals based on the syntenic relationship between cereals. Comparative mapping within families provides a method to the degree of sequence conservation, gene order, ploidy of species, ancestral relationships and the rates at which individual genomes are evolving. Comparative mapping has been carried out by cross-hybridizing molecular markers across species within a given family.

In a preferred embodiment, the nucleic acid molecules of the present invention can be utilized to isolate corresponding syntenic regions in non-rice plants (Bennetzen and Freeling, *Trends in Genet.,* 9(8):259-261 (1993); Ahn et al., *Mol. Gen. Genet.,* 241(5-6):483-490 (1993); Schwarzacher, *Cur. Opin. Genet. & Devel.,* 4(6): 868-874 (1994); Kurata et al., *Bio/Technology,* 12:276-278 (1994); Kilian et al., *Nucl. Acids Res.,* 23(14):2729-2733 (1995); Bennett, *Symp. Soc. Exp. Biol.,* 50:45-52 (1996); Hu et al., *Genetics,* 142(3):1021-1031 (1996); Kilian, *Plant Mol. Biol.,* 35:187-195 (1997); Bennetzen and Freeling, *Genome Res.,* 7(4):301-306 (1997); Foote et al., *Genetics,* 147(2):801-807 (1997); Gallego et al., *Genome,* 41(3):328-336 (1998)). Gale and Devos, *Proc. Natl. Acad. Sci. USA* 95:1971-1974 (1998); Bennetzen et al., *Proc. Natl. Acad. Sci. USA,* 95:1975-1978 (1998); Messing and Llaca, *Proc. Natl. Acad. Sci. USA* 95:2017-2020 (1998); McCouch, *Proc. Natl. Acad. Sci. USA,* 95:1983-1985 (1998); Goff, *Curr. Opin. Plant Biol.* 2:85-89 (1999); Bailey et al., *Theor. Appl. Genet.,* 98:281-284 (1999); Zhang et al., *Proc. Natl. Acad. Sci. USA,* 91:8675-8679 (1994); Yano and Sasaki, *Plant Mol. Biol.,* 35:145-153 (1997); Leister et al., *Proc. Natl. Acad. Sci. USA,* 95:370-375 (1998); Lin et al., *Phytopathology* 86(11):1156-1159 (1996); Havukkala, *Curr. Opin. Genet. Dev.,* 96:711-713 (1996); and Lee, *The Society for*

*Experimental Biology*, pp. 31-38 (1996), all of which are herein incorporated by reference in their entirety). Synteny between rice and barley has recently been reported in the genomic region carrying malting quality Quantitative Trait Loci (QTL) (Kleinhofs et al., *Genome* 41:373-380 (1998), the entirety of which is herein incorporated by reference). Likewise, mapping of the liguless region of sorghum, a region containing a developmental control gene, was facilitated using molecular markers from a syntenic region of the rice genome (Christou et al., *Genetics* 148:1983-1992 (1998), the entirety of which is herein incorporated by reference).

In a particularly preferred embodiment, the nucleic acid molecules of the present invention that define a genomic region in rice plants associated with a desirable phenotype are utilized to obtain corresponding syntenic regions in non-rice plants. A region can be defined either physically or genetically. In an even more preferred embodiment, the nucleic acid molecules of the present invention that define a genomic region in rice plants associated with a desirable phenotype are utilized to obtain corresponding syntenic regions in rice plants. A region can be defined either physically or genetically.

One or more of the nucleic acids molecules may be used to define a physical genomic region. For example, two nucleic acid molecules of the present invention can act to define a physical genomic region that lies between them. Moreover, for example, a physical genomic region may be defined by a distance relative to a nucleic acid molecule. In a preferred embodiment of the present invention, the defined physical genomic region is less than about 1,000 kb, more preferably less than about 500 kb, even more preferably less than about 100 kb or less than about 50 kb.

One or more of the nucleic acids molecules may be used to define a genomic region by its genetic distance from one or more nucleic acid molecules. In a preferred embodiment of the present invention, the genomic region is defined by its linkage to a nucleic acid molecule of the present invention. In such a preferred embodiment, the genomic region that is defined by one or more nucleic acid molecules of the present invention is located within about 50 centimorgans, more preferably within about 20 centimorgans, even more preferably with about 10, about 5 or about 2 centimorgans of the trait or marker at issue.

In another particularly preferred embodiment, two or more nucleic acid molecules of the present invention derived from rice plants that flank a genomic region of interest in rice plants are used to isolate the syntenic region in another cereal, more preferably maize, sorghum, barley, or wheat. Regions of interest in rice include, without limitation, those regions that are associated with a commercially desirable phenotype in rice. In another particularly preferred embodiment the desirable phenotype in rice is the result of a quantitative trait locus (QTL) present in the region.

One exemplary approach to isolate syntenic genomic regions is as follows. Nucleic acid molecules derived from rice of the present invention can be used to select large insert clones from a total genomic DNA library of a related species such as maize, sorghum, barley, or wheat. Any appropriate method to screen the genomic library with a nucleic acid molecule of the present invention may be used to select the required clones (See, for example, Birren et al., *Detecting Genes: A Laboratory Manual*, Cold Spring Harbor, New York, N.Y. (1998). For example, direct hybridization of a nucleic acid molecule of the present invention to mapping filters comprising the genomic DNA of the syntenic species can be used to select large insert clones from a total genomic DNA library of a related species. The selected clones can then be used to physically map the region in the target species. An advantage of this method for comparative mapping is that no mapping population or linkage map of the target species is needed and the clones may also be used in other closely related species. By comparing the results obtained by genetic mapping in model plants, with those from other species, similarities of genomic structure among plants species can be established. Cross-hybridization of RFLP markers have been reported and conserved gene order has been established in many studies. Such macroscopic synteny is utilized for the estimation of correspondence of loci among these crops. These loci include not only Mendelian genes but also Quantitative Trait Loci (QTL) (Mohan et al., *Molecular Breeding* 3:87-103 (1997), the entirety of which is herein incorporated by reference). Other methods to isolate syntenic nucleic acid molecules may be used.

It is understood that markers of the present invention may be used in comparative mapping. In a preferred embodiment the markers of present invention may be used in the comparative mapping of cereals, more preferably maize, barley, sorghum, and wheat.

It is understood that markers of the present invention may be used to isolate nucleic acid molecules from other cereals based on the syntenic relationship between such cereals. In a preferred embodiment the cereal is selected from the group of maize, sorghum, barley, and wheat.

The nucleic acid molecules of the present invention can be used to identify polymorphisms. In one embodiment, one or more of the nucleic acid molecules or a BAC nucleic acid molecule (or a sub-fragment of either) may be employed as a marker nucleic acid molecule to identify such polymorphism(s). Alternatively, such polymorphisms can be detected through the use of a marker nucleic acid molecule or a marker protein that is genetically linked to (i.e., a polynucleotide that co-segregates with) such polymorphism(s). In a preferred embodiment, the plant is selected from the group consisting of cereals, and more preferably rice, maize, barley, sorghum, and wheat.

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s), and more preferably within 100 kb of the polymorphism(s), and most preferably within 10 kb of the polymorphism(s) can be employed.

The genomes of animals and plants naturally undergo spontaneous mutation in the course of their continuing evolution (Gusella, *Ann. Rev. Biochem.* 55:831-854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e., the original "allele") whereas other members may have the variant sequence (i.e., the variant "allele"). In the simplest case, only one variant sequence may exist, and the polymorphism is thus said to be diallelic. In other cases, the species' population may contain multiple alleles, and the polymorphism is termed tri-allelic, etc. A single gene may have multiple different unrelated polymorphisms. For example, it may have a di-allelic polymorphism at one site, and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.* 307:113-115 (1992); Jones et al., *Eur. J. Haematol.* 39:144-147 (1987); Horn et al., PCT Application WO91/14003; Jeffreys, European Patent Application 370,719; Jeffreys, U.S. Pat. No. 5,175,082; Jeffreys et al., *Amer. J. Hum. Genet.* 39:11-24 (1986); Jeffreys et al., *Nature* 316:76-79 (1985); Gray et al., *Proc. R. Acad. Soc. Lond.* 243:241-253 (1991); Moore et al., *Genomics* 10:654-660 (1991); Jeffreys et al., *Anim. Genet.* 18:1-15 (1987); Hillel et al., *Anim. Genet.* 20:145-155 (1989); Hillel et al., *Genet.* 124:783-789 (1990), all of which are herein incorporated by reference in their entirety).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

The most preferred method of achieving such amplification employs the polymerase chain reaction ("PCR") (Mullis et al., *Cold Spring Harbor Symp. Quant. Biol.* 51:263-273 (1986); Erlich et al., European Patent Appln. 50,424; European Patent Appln. 84,796, European Patent Application 258,017, European Patent Appln. 237,362; Mullis, European Patent Appln. 201,184; Mullis, et al., U.S. Pat. No. 4,683,202; Erlich., U.S. Pat. No. 4,582,788; and Saiki et al., U.S. Pat. No. 4,683,194, all of which are herein incorporated by reference), using primer pairs that are capable of hybridizing to the proximal sequences that define a polymorphism in its double-stranded form.

In lieu of PCR, alternative methods, such as the "Ligase Chain Reaction" ("LCR") may be used (Barany, *Proc. Natl. Acad. Sci. USA* 88:189-193 (1991), the entirety of which is herein incorporated by reference). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069, the entirety of which is herein incorporated by reference).

The "Oligonucleotide Ligation Assay" ("OLA") may alternatively be employed (Landegren et al., *Science* 241:1077-1080 (1988), the entirety of which is herein incorporated by reference). The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson et al. have described a nucleic acid detection assay that combines attributes of PCR and OLA (Nickerson et al., *Proc. Natl. Acad. Sci. USA* 87:8923-8927 (1990), the entirety of which is herein incorporated by reference). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Schemes based on ligation of two (or more) oligonucleotides in the presence of nucleic acid having the sequence of the resulting "di-oligonucleotide", thereby amplifying the di-oligonucleotide, are also known (Wu et al., *Genomics* 4:560 (1989), the entirety of which is herein incorporated by reference), and may be readily adapted to the purposes of the present invention.

Other known nucleic acid amplification procedures, such as allele-specific oligomers, branched DNA technology, transcription-based amplification systems, or isothermal amplification methods may also be used to amplify and analyze such polymorphisms (Malek et al., U.S. Pat. No. 5,130,238; Davey et al., European Patent Application 329,822; Schuster et al., U.S. Pat. No. 5,169,766; Miller et al., PCT Application WO 89/06700; Kwoh et al., *Proc. Natl. Acad. Sci. USA* 86:1173-1177 (1989); Gingeras et al., PCT Application WO 88/10315; Walker et al., *Proc. Natl. Acad. Sci. USA* 89:392-396 (1992), all of which are herein incorporated by reference in their entirety).

The identification of a polymorphism can be determined in a variety of ways. By correlating the presence or absence of it in an plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and plant genetic analyses (Glassberg, UK Patent Application 2135774; Skolnick et al., *Cytogen. Cell Genet.* 32:58-67 (1982); Botstein et al., *Ann. J. Hum. Genet.* 32:314-331 (1980); Fischer et al. PCT Application WO90/13668; Uhlen, PCT Application WO90/11369).

Polymorphisms can also be identified by Single Strand Conformation Polymorphism (SSCP) analysis. The SSCP technique is a method capable of identifying most sequence variations in a single strand of DNA, typically between 150 and 250 nucleotides in length (Elles, *Methods in Molecular Medicine: Molecular Diagnosis of Genetic Diseases*, Humana Press (1996); Orita et al., *Genomics* 5:874-879 (1989), both of which are herein incorporated by reference in their entirety). Under denaturing conditions a single strand of DNA will adopt a conformation that is uniquely dependent on its sequence conformation. This conformation usually will be different, even if only a single base is changed. Most conformations have been reported to alter the physical configuration or size sufficiently to be detectable by electrophoresis. A number of protocols have been described for SSCP including, but not limited to Lee et al., *Anal. Biochem.* 205:289-293 (1992); Suzuki et al., *Anal. Biochem.* 192:82-84 (1991); Lo et al., *Nucleic Acids Research* 20:1005-1009 (1992); Sarkar et al., *Genomics* 13:441-443 (1992), all of which are herein incorporated by reference in their entirety). It is understood that one or more of the nucleic acids of the present invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA. Vos et al., *Nucleic Acids Res.* 23:4407-4414 (1995), the entirety of which is herein incorporated by reference. This method allows for the specific co-amplification of high numbers of restriction fragments, which can be visualized by PCR without knowledge of the nucleic acid sequence.

AFLP employs basically three steps. Initially, a sample of genomic DNA is cut with restriction enzymes and oligonucleotide adapters are ligated to the restriction fragments of the DNA. The restriction fragments are then amplified using PCR by using the adapter and restriction sequence as target sites for primer annealing. The selective amplification is achieved by the use of primers that extend into the restriction fragments, amplifying only those fragments in which the primer extensions match the nucleotide flanking the restriction sites. These amplified fragments are then visualized on a denaturing polyacrylamide gel.

AFLP analysis has been performed on *Salix* (Beismann et al., *Mol. Ecol.* 6:989-993 (1997), the entirety of which is herein incorporated by reference); *Acinetobacter* (Janssen et al., *Int. J. Syst. Bacteriol* 47:1179-1187 (1997), the entirety of which is herein incorporated by reference), *Aeromonas popoffi* (Huys et al., *Int. J. Syst. Bacteriol.* 47:1165-1171 (1997), the entirety of which is herein incorporated by reference), rice (McCouch et al., *Plant Mol. Biol.* 35:89-99 (1997); Nandi et al., *Mol. Gen. Genet.* 255:1-8 (1997); Cho et al., *Genome* 39:373-378 (1996), all of which are herein incorporated by reference in their entirety), barley (*Hordeum vulgare*) (Simons et al., *Genomics* 44:61-70 (1997); Waugh et al., *Mol. Gen. Genet.* 255:311-321 (1997); Qi et al., *Mol. Gen. Genet.* 254:330-336 (1997); Becker et al., *Mol. Gen. Genet.* 249:65-73 (1995), all of which are herein incorporated by reference in their entirety), potato (Van der Voort et al., *Mol. Gen. Genet.* 255:438-447 (1997); Meksem et al., *Mol. Gen. Genet.* 249:74-81 (1995), both of which are herein incorporated by reference in their entirety), *Phytophthora infestans* (Van der Lee et al., *Fungal Genet. Biol.* 21:278-291 (1997), the entirety of which is herein incorporated by reference), *Bacillus anthracis* (Keim et al., *J. Bacteriol.* 179:818-824 (1997)), *Astragalus cremnophylax* (Travis et al., *Mol. Ecol.* 5:735-745 (1996), the entirety of which is herein incorporated by reference), *Arabidopsis* (Cnops et al., *Mol. Gen. Genet.* 253:32-41 (1996), the entirety of which is herein incorporated by reference), *Escherichia coli* (Lin et al., *Nucleic Acids Res.* 24:3649-3650 (1996), the entirety of which is herein incorporated by reference), *Aeromonas* (Huys et al., *Int. J. Syst. Bacteriol.* 46:572-580 (1996), the entirety of which is herein incorporated by reference), nematode (Folkertsma et al., *Mol. Plant Microbe Interact.* 9:47-54 (1996), the entirety of which is herein incorporated by reference), tomato (Thomas et al., *Plant J.* 8:785-794 (1995), the entirety of which is herein incorporated by reference), and human (Latorra et al., *PCR Methods Appl.* 3:351-358 (1994) the entirety of which is herein incorporated by reference). AFLP analysis has also been used for fingerprinting mRNA (Money et al., *Nucleic Acids Res.* 24:2616-2617 (1996); Bachem, et al., *Plant J.* 9:745-753 (1996), both of which are herein incorporated by reference in their entirety). It is understood that one or more of the nucleic acid molecules of the present invention, may be utilized as markers or probes to detect polymorphisms by AFLP analysis for fingerprinting mRNA.

Polymorphisms may also be found using random amplified polymorphic DNA (RAPD) (Williams et al., *Nucl. Acids Res.* 18:6531-6535 (1990), the entirety of which is herein incorporated by reference) and cleavable amplified polymorphic sequences (CAPS) (Lyamichev et al., *Science* 260:778-783 (1993), the entirety of which is herein incorporated by reference). It is understood that one or more of the nucleic acid molecules of the present invention, may be utilized as markers or probes to detect polymorphisms by RAPD or CAPS analysis.

Nucleic acid molecules of the present invention can be used to monitor expression. A microarray-based method for high-throughput monitoring of plant gene expression may be utilized to measure gene-specific hybridization targets. This 'chip'-based approach involves using microarrays of nucleic acid molecules as gene-specific hybridization targets to quantitatively measure expression of the corresponding plant genes (Schena et al., *Science* 270:467-470 (1995); Shalon, Ph.D. Thesis. Stanford University (1996), both of which are herein incorporated by reference in their entirety). Every nucleotide in a large sequence can be queried at the same time. Hybridization can be used to efficiently analyze nucleotide sequences.

Several microarray methods have been described. One method compares the sequences to be analyzed by hybridization to a set of oligonucleotides or cDNA molecules representing all possible subsequences (Bains and Smith, *J. Theor. Biol.* 135:303 (1989), the entirety of which is herein incorporated by reference). A second method hybridizes the sample to an array of oligonucleotide or cDNA probes. An array consisting of oligonucleotides or cDNA molecules complementary to subsequences of a target sequence can be used to determine the identity of a target sequence, measure its amount, and detect differences between the target and a reference sequence. Nucleic acid molecule microarrays may also be screened with protein molecules or fragments thereof to determine nucleic acid molecules that specifically bind protein molecules or fragments thereof.

Additionally, microarrays of BACs may be prepared to sufficiently cover 3× of an entire genome. Such microarrays can be used in a variety of genomics experiments including gene mapping, DNA fingerprinting and promoter identification. Microarrays of genomic DNA can also be used for parallel analysis of genomes at single gene resolution (Lemieux et al., *Molecular Breeding* 277-289 (1988), the entirety of which is herein incorporated by reference). It is understood that one or more of the molecules of the present invention, preferably one or more of the nucleic acid molecules or protein molecules or fragments thereof of the present invention may be utilized in a genomic microarray based method. In a preferred embodiment of the present invention, one or more of the rice nucleic acid molecules or protein molecules or fragments thereof of the present invention may be utilized in a genomic microarray based method. For example, Genomic Mismatch Scanning (GMS), a hybridization-based method of linkage analysis that allows rapid identification of regions of identity-by-descent between two related individuals, can be carried out with microarrays. GMS is reported to have been used to identify genetically common chromosomal segments based on the ability of these DNA sequences to form extensive regions of mismatch-free heteroduplexes. A series of enzymatic steps, coupled with filter binding, is used to selectively remove heteroduplexes that contain mismatches (i.e., chromosomal regions that do not share identity-by-descent.). Fragments of chromosomal DNA representing inherited regions are hybridized to a microarray of ordered genomic clones and positive hybridization signals pinpoint regions of identity-by-descent at high resolution (Lemieux et al., *Molecular Breeding* 277-289 (1988)).

It is understood that one or more of the molecules of the present invention, preferably one or more of the nucleic acid molecules or protein molecules or fragments thereof of the present invention may be utilized in a GMS microarray based method to locate regions of identity-by-descent between related individuals. In a preferred embodiment of the present invention, one or more of the rice nucleic acid molecules or protein molecules or fragments thereof of the present invention may be utilized in a GMS microarray based method to locate regions of identity-by-descent between related individuals. The GMS microarray approach can also be used as a tool to map multigenic traits. For example, in yeast, the entire genomic sequence is known and it has been reported that the genes responsible for growth at elevated temperature, a trait required for the pathogenicity of certain yeast strains, may be determined using GMS (Lemieux et al., *Molecular Breeding* 277-289 (1988)). By analyzing the inheritance of large numbers of tetrads derived from crosses of pathogenic and wild type strains, all the genes responsible for a yeast strain's ability to grow at 42° C., for example, could be identified.

It is understood that one or more of the molecules of the present invention, preferably one or more of the nucleic acid molecules or protein molecules or fragments thereof of the present invention may be utilized in a GMS microarray based method to map multigenic traits. In a preferred embodiment of the present invention, one or more of the rice nucleic acid molecules or protein molecules or fragments thereof of the present invention may be utilized in a GMS microarray based method to map multigenic traits.

Plant repeat elements may be used with GMS microarraying to identify species specific chromosomes in another species background. For example, the maize genome contains moderately repetitive DNA sequences (ZLRS) representing about 2500 copies per haploid genome; these sequences are present in the genus *Zea* and absent in other graminaceous species. Ananiev et al., *Proc. Natl. Acad. Sci. USA* 94:3526-3529 (1997), the entirety of which is herein incorporated by reference, have reported unusual plants with individual maize chromosomes added to a complete oat genome generated by embryo rescue from oat (*Avena sativa*)×*Zea mays* crosses. By using highly repetitive maize-specific sequences as probes, Ananiev et al., *Proc. Natl. Acad. Sci. USA* 94:3526-3529 (1997) were able to selectively isolate cosmid clones containing maize genomic DNA.

It is understood that one or more of the molecules of the present invention, preferably one or more of the nucleic acid molecules or protein molecules or fragments thereof of the present invention may be utilized in a GMS microarray based method using repeat elements to selectively isolate clones containing species specific DNA. In a preferred embodiment of the present invention, one or more of the rice nucleic acid molecules or protein molecules or fragments thereof of the present invention may be utilized in a GMS microarray based method to selectively isolate clones containing species specific DNA. A particularly preferred microarray embodiment of the present invention is a microarray comprising nucleic acid molecules encoding genes that are homologues of known genes or nucleic acid molecules that comprise genes or fragments thereof that elicit only limited or no matches to known genes. A further preferred microarray embodiment of the present invention is a microarray comprising nucleic acid molecules encoding genes or fragments thereof that are homologues of known genes and nucleic acid molecules that comprise genes or fragments thereof that elicit only limited or no matches to known genes. A further preferred microarray embodiment of the present invention is a microarray comprising nucleic acid molecules encoding genes or fragments thereof that elicit only limited or no matches to known genes.

It is understood that one or more of the molecules of the present invention, preferably one or more of the nucleic acid molecules or protein molecules or fragments thereof of the present invention may be utilized in a microarray based method.

In a preferred embodiment of the present invention, one or more of the nucleic acid molecules or protein molecules or fragments thereof or other agents of the present invention may be utilized in a microarray based method.

Nucleic acid molecules of the present invention may be used in site directed mutagenesis. Site-directed mutagenesis may be utilized to modify nucleic acid sequences, particularly as it is a technique that allows one or more of the amino acids encoded by a nucleic acid molecule to be altered (e.g., a threonine to be replaced by a methionine). Three basic methods for site-directed mutagenesis are often employed. These are cassette mutagenesis (Wells et al., *Gene* 34:315-23 (1985), the entirety of which is herein incorporated by reference), primer extension (Gilliam et al., *Gene* 12:129-137 (1980); Zoller and Smith, *Methods Enzymol.* 100:468-500 (1983); and Dalbadie-McFarland et al., *Proc. Natl. Acad. Sci. USA* 79:6409-6413 (1982), all of which are herein incorporated by reference in their entirety) and methods based upon PCR (Scharf et al., *Science* 233:1076-1078 (1986); Higuchi et al., *Nucleic Acids Res.* 16:7351-7367 (1988), both of which are herein incorporated by reference in their entirety). Site-directed mutagenesis approaches are also described in European Patent 0 385 962, European Patent 0 359 472, and PCT Patent Application WO 93/07278, all of which are herein incorporated by reference in their entirety.

Site-directed mutagenesis strategies have been applied to plants for both in vitro as well as in vivo site-directed mutagenesis (Lanz et al., *J. Biol. Chem.* 266:9971-6 (1991); Kovgan and Zhdanov, *Biotekhnologiya* 5:148-154, No. 207160n, Chemical Abstracts 110:225 (1989); Ge et al., *Proc. Natl. Acad. Sci. USA* 86:4037-4041 (1989); Zhu et al., *J. Biol. Chem.* 271:18494-18498 (1996), Chu et al., *Biochemistry* 33:6150-6157 (1994); Small et al., *EMBO J.* 11:1291-1296 (1992); Cho et al., *Mol. Biotechnol.* 8:13-16 (1997), Kita et al., *J. Biol. Chem.* 271:26529-26535 (1996); Jin et al., *Mol. Microbiol.* 7:555-562 (1993); Hatfield and Vierstra, *J. Biol. Chem.* 267:14799-14803 (1992); Zhao et al., *Biochemistry* 31:5093-5099 (1992), all of which are herein incorporated by reference in their entirety).

Any of the nucleic acid molecules of the present invention may either be modified by site-directed mutagenesis or used as, for example, nucleic acid molecules that are used to target other nucleic acid molecules for modification. It is understood that mutants with more than one altered nucleotide can be constructed using techniques that practitioners skilled in the art are familiar with such as isolating restriction fragments and ligating such fragments into an expression vector (see, for example, Sambrook et al., *Molecular Cloning: A Laboratory Manual*, Cold Spring Harbor Press (1989)). In a preferred embodiment of the present invention, one or more of the rice nucleic acid molecules or fragments thereof of the present invention may be modified by site-directed mutagenesis.

Nucleic acid molecules of the present invention may be used in transformation. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. In a preferred embodiment of the present invention the exogenous genetic material can include rice genetic material. A particularly preferred embodiment is exogenous genetic material that comprises a nucleic acid molecule of the present invention. Such genetic material may be transferred into either monocotyledons and dicotyledons including but not limited to the plants, maize and *Arabidopsis thaliana* and rice (See specifically, Chistou, *Particle Bombardment for Genetic Engineering of plants*, pp. 63-69 (maize), pp 50-60 (rice), Biotechnology Intelligence Unit, Academic Press, San Diego, Calif. (1996), the entirety of which is herein incorporated by reference and generally Chistou, *Particle Bombardment for Genetic Engineering of Plants*, Biotechnology Intelligence Unit, Academic Press, San Diego, Calif. (1996), the entirety of which is herein incorporated by reference).

Transfer of a nucleic acid that encodes for a protein can result in overexpression of that protein in a transformed cell or transgenic plant. One or more of the proteins or fragments thereof encoded by nucleic acid molecules of the present invention may be overexpressed in a transformed cell or transformed plant. Such overexpression may be the result of transient or stable transfer of the exogenous material.

Exogenous genetic material may be transferred into a plant cell by the use of a DNA vector or construct designed for such a purpose. Preferred exogenous genetic material comprise a nucleic acid molecule of the present invention. Vectors have been engineered for transformation of large DNA inserts into plant genomes. Vectors have been designed to replicate in both *E. coli* and *A. tumefaciens* and have all of the features required for transferring large inserts of DNA into plant chromosomes (Choi and Wing, at the website genome.clemson-.edu/protocols2-nj.html July, 1998). ApBACwich system has been developed to achieve site-directed integration of DNA into the genome. A 150 kb cotton BAC DNA is reported to have been transferred into a specific lox site in tobacco by biolistic bombardment and Cre-lox site specific recombination.

A construct or vector may include a plant promoter to express the protein or protein fragment of choice. A number of promoters which are active in plant cells have been described in the literature. These include the nopaline synthase (NOS) promoter (Ebert et al., *Proc. Natl. Acad. Sci. USA* 84:5745-5749 (1987), the entirety of which is herein incorporated by reference), the octopine synthase (OCS) promoter (which are carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987), the entirety of which is herein incorporated by reference) and the CaMV 35S promoter (Odell et al., *Nature* 313:810-812 (1985), the entirety of which is herein incorporated by reference), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci. USA* 84:6624-6628 (1987), the entirety of which is herein incorporated by reference), the sucrose synthase promoter (Yang et al., *Proc. Natl. Acad. Sci. USA* 87:4144-4148 (1990), the entirety of which is herein incorporated by reference), the R gene complex promoter (Chandler et al., *The Plant Cell* 1:1175-1183 (1989), the entirety of which is herein incorporated by reference), and the chlorophyll a/b binding protein gene promoter, etc. These promoters have been used to create DNA constructs which have been expressed in plants; see, e.g., PCT publication WO 84/02913, herein incorporated by reference in its entirety.

Promoters which are known or are found to cause transcription of DNA in plant cells can be used in the present invention. Such promoters may be obtained from a variety of sources such as plants and plant viruses. It is preferred that the particular promoter selected should be capable of causing sufficient expression to result in the production of an effective amount of protein to cause the desired phenotype. In addition to promoters which are known to cause transcription of DNA in plant cells, other promoters may be identified for use in the current invention by screening a plant cDNA library for genes which are selectively or preferably expressed in the target tissues or cells.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea (Edwards et al., *Proc. Natl. Acad. Sci. USA* 87:3459-3463 (1990), herein incorporated by reference in its entirety), the chloroplast fructose-1,6-biphosphatase (FBPase) promoter from wheat (Lloyd et al., *Mol. Gen. Genet.* 225:209-216 (1991), herein incorporated by reference in its entirety), the nuclear photosynthetic ST-LS1 promoter from potato (Stockhaus et al., *EMBO J.* 8:2445-2451 (1989), herein incorporated by reference in its entirety), the phenylalanine ammonia-lyase (PAL) promoter and the chalcone synthase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773-778 (1994), herein incorporated by reference in its entirety), the promoter for the Cab-1 gene from wheat (Fejes et al., *Plant Mol. Biol.* 15:921-932 (1990), herein incorporated by reference in its entirety), the promoter for the CAB-1 gene from spinach (Lubberstedt et al., *Plant Physiol.* 104:997-1006 (1994), herein incorporated by reference in its entirety), the promoter for the cab1R gene from rice (Luan et al., *Plant Cell.* 4:971-981 (1992), the entirety of which is herein incorporated by reference), the pyruvate, orthophosphate dikinase (PPDK) promoter from maize (Matsuoka et al., *Proc. Natl. Acad. Sci. USA* 90:9586-9590 (1993), herein incorporated by reference in its entirety), the promoter for the tobacco Lhcb1*2 gene (Cerdan et al., *Plant Mol Biol.* 33:245-255. (1997), herein incorporated by reference in its entirety), the *Arabidopsis thaliana* SUC2 sucrose-H+ symporter promoter (Truernit et al., *Planta.* 196:564-570 (1995), herein incorporated by reference in its entirety), and the promoter for the thylacoid membrane proteins from spinach (psaD, psaF, psaE, PC, FNR, atpC, atpD, cab, rbcS). Other promoters for the chlorophyll a/b-binding proteins may also be utilized in the present invention, such as the promoters for LhcB gene and PsbP gene from white mustard (Sinapis alba; Kretsch et al., *Plant Mol. Biol.* 28:219-229 (1995), the entirety of which is herein incorporated by reference).

For the purpose of expression in sink tissues of the plant, such as the tuber of the potato plant, the fruit of tomato, or the seed of maize, wheat, rice, and barley, it is preferred that the promoters utilized in the present invention have relatively high expression in these specific tissues. A number of promoters for genes with tuber-specific or -enhanced expression are known, including the class I patatin promoter (Bevan et al., *EMBO J.* 8:1899-1906 (1986); Jefferson et al., *Plant Mol. Biol.* 14995-1006 (1990), both of which are herein incorporated by reference in its entirety), the promoter for the potato tuber ADPGPP genes, both the large and small subunits, the sucrose synthase promoter (Salanoubat and Belliard, *Gene.* 60:47-56 (1987), Salanoubat and Belliard, *Gene.* 84:181-185 (1989), both of which are incorporated by reference in their entirety), the promoter for the major tuber proteins including the 22 kd protein complexes and proteinase inhibitors (Hannapel, *Plant Physiol.* 101:703-704 (1993), herein incorporated by reference in its entirety), the promoter for the granule bound starch synthase gene (GBSS) (Visser et al., *Plant Mol. Biol.* 17:691-699 (1991), herein incorporated by reference in its entirety), and other class I and II patatins promoters (Koster-Topfer et al., *Mol. Gen. Genet.* 219:390-396 (1989); Mignery et al., *Gene.* 62:27-44 (1988), both of which are herein incorporated by reference in their entirety).

Other promoters can also be used to express a fructose 1,6 bisphosphate aldolase gene in specific tissues, such as seeds or fruits. The promoter for β-conglycinin (Chen et al., *Dev. Genet.* 10:112-122 (1989), herein incorporated by reference in its entirety) or other seed-specific promoters such as the napin and phaseolin promoters, can be used. The zeins are a group of storage proteins found in maize endosperm. Genomic clones for zein genes have been isolated (Pedersen et al., *Cell* 29:1015-1026 (1982), herein incorporated by reference in its entirety), and the promoters from these clones, including the 15 kD, 16 kD, 19 kD, 22 kD, 27 kD, and gamma genes, could also be used. Other promoters known to function, for example, in maize, include the promoters for the following genes: waxy, *Brittle, Shrunken* 2, Branching enzymes I and II, starch synthases, debranching enzymes, oleosins, glutelins, and sucrose synthases. A particularly preferred promoter for maize endosperm expression is the promoter for the glutelin gene from rice, more particularly the Osgt-1 promoter (Zheng et al., *Mol. Cell Biol.* 13:5829-5842 (1993), herein incorporated by reference in its entirety). Examples of promoters suitable for expression in wheat include those promoters for the ADPglucose pyrophosphorylase (ADPGPP) subunits, the granule bound and other starch synthases, the branching and debranching enzymes, the embryogenesis-abundant proteins, the gliadins, and the glutenins. Examples of such promoters in rice include those promoters for the ADPGPP subunits, the granule bound and other starch synthases, the branching enzymes, the debranching enzymes, sucrose synthases, and the glutelins. A particularly preferred promoter is the promoter for rice glutelin, Osgt-1. Examples of such promoters for barley include those for the ADPGPP subunits, the granule bound and other starch synthases, the branching enzymes, the debranching enzymes, sucrose synthases, the hordeins, the embryo globulins, and the aleurone specific proteins.

Root specific promoters may also be used. An example of such a promoter is the promoter for the acid chitinase gene (Samac et al., *Plant Mol. Biol* 25:587-596 (1994), the entirety of which is herein incorporated by reference). Expression in root tissue could also be accomplished by utilizing the root specific subdomains of the CaMV35S promoter that have been identified (Lam et al., *Proc. Natl. Acad. Sci. USA* 86:7890-7894 (1989), herein incorporated by reference in its entirety). Other root cell specific promoters include those reported by Conkling et al. (Conkling et al., *Plant Physiol.* 93:1203-1211 (1990), the entirety of which is herein incorporated by reference).

Additional promoters that may be utilized are described, for example, in U.S. Pat. Nos. 5,378,619, 5,391,725, 5,428,147, 5,447,858, 5,608,144, 5,608,144, 5,614,399, 5,633,441, 5,633,435, and 4,633,436, all of which are herein incorporated in their entirety. In addition, a tissue specific enhancer may be used (Fromm et al., *The Plant Cell* 1:977-984 (1989), the entirety of which is herein incorporated by reference).

Constructs or vectors may also include, with the coding region of interest, a nucleic acid sequence that acts, in whole or in part, to terminate transcription of that region. For example, such sequences have been isolated including the Tr7 3' sequence and the nos 3' sequence (Ingelbrecht et al., *The Plant Cell* 1:671-680 (1989); Bevan et al., *Nucleic Acids Res.* 11:369-385 (1983), both of which are herein incorporated by reference in their entirety), or the like.

A vector or construct may also include regulatory elements. Examples of such include the Adh intron 1 (Callis et al., *Genes and Develop.* 1:1183-1200 (1987), the entirety of which is herein incorporated by reference), the sucrose synthase intron (Vasil et al., *Plant Physiol.* 91:1575-1579 (1989), the entirety of which is herein incorporated by reference) and the TMV omega element (Gallie et al., *The Plant Cell* 1:301-311 (1989), the entirety of which is herein incorporated by reference). These and other regulatory elements may be included when appropriate.

A vector or construct may also include a selectable marker. Selectable markers may also be used to select for plants or plant cells that contain the exogenous genetic material. Examples of such include, but are not limited to, a neo gene (Potrykus et al., *Mol. Gen. Genet.* 199:183-188 (1985), the entirety of which is herein incorporated by reference) which codes for kanamycin resistance and can be selected for using kanamycin, G418, etc.; a bar gene which codes for bialaphos resistance; a mutant EPSP synthase gene (Hinchee et al., *Bio/Technology* 6:915-922 (1988), the entirety of which is herein incorporated by reference) which encodes glyphosate resistance; a nitrilase gene which confers resistance to bromoxynil (Stalker et al., *J. Biol. Chem.* 263:6310-6314 (1988), the entirety of which is herein incorporated by reference); a mutant acetolactate synthase gene (ALS) which confers imidazolinone or sulphonylurea resistance (European Patent Application 154,204 (Sep. 11, 1985), the entirety of which is herein incorporated by reference); and a methotrexate resistant DHFR gene (Thillet et al., *J. Biol. Chem.* 263:12500-12508 (1988), the entirety of which is herein incorporated by reference).

A vector or construct may also include a transit peptide. Incorporation of a suitable chloroplast transit peptide may also be employed (European Patent Application Publication Number 0218571, the entirety of which is herein incorporated by reference). Translational enhancers may also be incorporated as part of the vector DNA. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393-405 (1996), the entirety of which is herein incorporated by reference.

A vector or construct may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405 (1987); Jefferson et al., *EMBO J.* 6:3901-3907 (1987), both of which are herein incorporated by reference in their entirety); an R-locus gene, which encodes a product that regulates the production of anthocyanin pigments (red color) in plant tissues ((Dellaporta et al., Stadler Symposium 11:263-282 (1988), the entirety of which is herein incorporated by reference); a β-lactamase gene (Sutcliffe et al., *Proc. Natl. Acad. Sci. USA* 75:3737-3741 (1978), the entirety of which is herein incorporated by reference), a gene which encodes an enzyme for which various chromogenic substrates are known (e.g., PADAC, a chromogenic cephalosporin); a luciferase gene (Ow et al., *Science* 234: 856-859 (1986), the entirety of which is herein incorporated by reference) a xylE gene (Zukowsky et al., *Proc. Natl. Acad. Sci. USA* 80:1101-1105 (1983), the entirety of which is herein incorporated by reference) which encodes a catechol dioxygenase that can convert chromogenic catechols; an α-amylase gene (Ikatu et al., *Bio/Technol.* 8:241-242 (1990), the entirety of which is herein incorporated by reference); a tyrosinase gene (Katz et al., *J. Gen. Microbiol.* 129:2703-2714 (1983), the entirety of which is herein incorporated by reference) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

Methods and compositions for transforming a bacteria and other microorganisms are known in the art (see for example Sambrook et al., *Molecular Cloning: A Laboratory Manual*, Second Edition, Cold Spring Harbor Laboratory Press, Cold Spring Harbor, N.Y., (1989), the entirety of which is herein incorporated by reference).

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, etc. (Pottykus, *Ann. Rev. Plant Physiol. Plant Mol. Biol.* 42:205-225 (1991); Vasil, *Plant Mol. Biol.* 25:925-937 (1994), both of which are herein incorporated by reference in their entirety). For example, electroporation has been used to transform maize protoplasts (Fromm et al., *Nature* 312:791-793 (1986), the entirety of which is herein incorporated by reference).

Technology for introduction of DNA into cells is well known to those of skill in the art. Four general methods for delivering a gene into cells have been described: (1) chemical methods (Graham and van der Eb, *Virology*, 54:536-539 (1973), the entirety of which is herein incorporated by reference); (2) physical methods such as microinjection (Capecchi, *Cell* 22:479-488 (1980), electroporation (Wong and Neumann, *Biochem. Biophys. Res. Commun.*, 107:584-587 (1982); Fromm et al., *Proc. Natl. Acad. Sci. USA*, 82:5824-5828 (1985); U.S. Pat. No. 5,384,253; and the gene gun (Johnston and Tang, *Methods Cell Biol.* 43:353-365 (1994), all of which are herein incorporated by reference in their entirety; (3) viral vectors (Clapp, *Clin. Perinatol.*, 20:155-168 (1993); Lu et al., *J. Exp. Med.*, 178:2089-2096 (1993); Eglitis and Anderson, *Biotechniques*, 6:608-614 (1988), all of which are herein incorporated by reference in their entirety); and (4) receptor-mediated mechanisms (Curiel et al., *Hum. Gen. Ther.*, 3:147-154 (1992); Wagner et al., *Proc. Natl. Acad. Sci. USA*, 89:6099-6103 (1992), all of are herein incorporated by reference in their entirety).

Acceleration methods that may be used include, for example, microprojectile bombardment and the like. One example of a method for delivering transforming nucleic acid molecules to plant cells is microprojectile bombardment. This method has been reviewed by Yang and Christou, eds., *Particle Bombardment Technology for Gene Transfer*, Oxford Press, Oxford, England (1994), the entirety of which is herein incorporated by reference). Non-biological particles (microprojectiles) that may be coated with nucleic acids and delivered into cells by a propelling force. Exemplary particles include those comprised of tungsten, gold, platinum, and the like.

A particular advantage of microprojectile bombardment, in addition to it being an effective means of reproducibly, and stably transforming monocotyledons, is that neither the isolation of protoplasts (Cristou et al., *Plant Physiol.* 87:671-674 (1988), the entirety of which is herein incorporated by reference) nor the susceptibility of *Agrobacterium* infection is required. An illustrative embodiment of a method for delivering DNA into maize cells by acceleration is a biolistics-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603-618 (1990), the entirety of which is herein incorporated by reference). The screen disperses the tungsten nucleic acid particles so that they are not delivered to the recipient cells in large aggregates. A particle delivery system suitable for use with the present invention is the helium acceleration PDS-1000/He gun which is available from Bio-Rad Laboratories (Bio-Rad, Hercules, Calif. et al., *Technique* 3:3-16 (1991), the entirety of which is herein incorporated by reference).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from one to ten and average one to three.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include particle gun delivery of DNA containing a selectable marker and targeting of the DNA to the plastid genome through homologous recombination (Svab et al. *Proc. Natl. Acad. Sci. USA* 87:8526-8530 (1990); Svab and Maliga *Proc. Natl. Acad. Sci. USA* 90:913-917 (1993)); Staub, J. M. and Maliga, P. *EMBO J.* 12:601-606 (1993), U.S. Pat. Nos. 5,451,513 and 5,545,818, all of which are herein incorporated by reference in their entirety).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described (Fraley et al., *Biotechnology* 3:629-635 (1985); Rogers et al., *Meth. In Enzymol*, 153:253-277 (1987), both of which are herein incorporated by reference in their entirety). Further, the integration of the Ti-DNA is a relatively precise process resulting in few rearrangements. The region of DNA to be transferred is defined by the border sequences, and intervening DNA is usually inserted into the plant genome as described (Spielmann et al., *Mol. Gen. Genet.*, 205:34 (1986), the entirety of which is herein incorporated by reference).

Modern *Agrobacterium* transformation vectors are capable of replication in *E. coli* as well as *Agrobacterium*, allowing for convenient manipulations as described (Klee et al., In: *Plant DNA Infectious Agents*, T. Hohn and J. Schell, eds., Springer-Verlag, New York, pp. 179-203 (1985), the entirety of which is herein incorporated by reference). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Meth. In Enzymol.*, 153:253-277 (1987), the entirety of which is herein incorporated by reference). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for the gene of interest.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation, and combinations of these treatments. See for example (Potrykus et al., *Mol. Gen. Genet.*, 205:193-200 (1986); Lorz et al., *Mol. Gen. Genet.*, 199:178, (1985); Fromm et al., *Nature*, 319:791, (1986); Uchimiya et al., *Mol. Gen. Genet.:*204:204, (1986); Callis et al., *Genes and Development*, 1183, (1987); Marcotte et al., *Nature*, 335:454, (1988), all of which the entirety is herein incorporated by reference).

Application of these systems to different plant strains depends upon the ability to regenerate that particular plant strain from protoplasts. Illustrative methods for the regeneration of cereals from protoplasts are described (Fujimura et al., *Plant Tissue Culture Letters*, 2:74, (1985); Toriyama et al., *Theor Appl. Genet.* 205:34. (1986); Yamada et al., *Plant Cell Rep.*, 4:85, (1986); Abdullah et al., *Biotechnology*, 4:1087, (1986), all of which the entirety is herein incorporated by reference).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology*, 6:397, (1988), the entirety of which is herein incorporated by reference). In addition, "particle gun" or high-velocity microprojectile technology can be utilized (Vasil et al., *Bio/Technology* 10:667, (1992), the entirety of which is herein incorporated by reference).

Using the latter technology, DNA is carried through the cell wall and into the cytoplasm on the surface of small metal particles as described (Klein et al., *Nature*, 328:70, (1987); Klein et al., *Proc. Natl. Acad. Sci. USA*, 85:8502-8505, (1988); McCabe et al., *Biotechnology*, 6:923, (1988), all of which the entirety is herein incorporated by reference). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol.*, 107:367, (1987); Luo et al., *Plant Mol. Biol. Reporter*, 6:165, (1988), all of which the entirety is herein incorporated by reference), by direct injection of DNA into reproductive organs of a plant (Pena et al., *Nature*, 325:274, (1987), the entirety of which is herein incorporated by reference), or by direct injection of DNA into the cells of immature embryos followed by the rehydration of desiccated embryos (Neuhaus et al., *Theor. Appl. Genet.*, 75:30, (1987), the entirety of which is herein incorporated by reference).

The regeneration, development, and cultivation of plants from single plant protoplast transformants or from various transformed explants is well known in the art (Weissbach and Weissbach, In: *Methods for Plant Molecular Biology*, (Eds.), Academic Press, Inc., San Diego, Calif., (1988), the entirety of which is herein incorporated by reference). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants, as discussed before. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908, all of which the entirety is herein incorporated by reference); rice (U.S. Pat. No. 5,569,834, U.S. Pat. No. 5,416,011, McCabe et al., *Biotechnology* 6:923, (1988), Christou et al., *Plant Physiol.*, 87:671-674 (1988), all of which the entirety is herein incorporated by reference); *Brassica* (U.S. Pat. No. 5,463,174, the entirety of which is herein incorporated by reference); peanut (Cheng et al., *Plant Cell Rep.* 15:653-657 (1996), McKently et al., *Plant Cell Rep.* 14:699-703 (1995), all of which the entirety is herein incorporated by reference); papaya (Yang et al., (1996), the entirety of which is herein incorporated by reference); pea (Grant et al., *Plant Cell Rep.* 15:254-258, (1995), the entirety of which is herein incorporated by reference).

Transformation of monocotyledons using electroporation, particle bombardment, and *Agrobacterium* have also been reported. Transformation and plant regeneration have been achieved in asparagus (Bytebier et al., *Proc. Natl. Acad. Sci. USA* 84:5345, (1987), the entirety of which is herein incorporated by reference); barley (Wan and Lemaux, *Plant Physiol* 104:37, (1994), the entirety of which is herein incorporated by reference); maize (Rhodes et al., *Science* 240:204, (1988), Gordon-Kamm et al., *Plant Cell*, 2:603, (1990), Fromm et al., *Bio/Technology* 8:833, (1990), Koziel et al., *Bio/Technology* 11:194, (1993), Armstrong et al., *Crop Science* 35:550-557, (1995), all of which the entirety is herein incorporated by reference); oat (Somers et al., *Bio/Technology*, 10:1589, (1992), the entirety of which is herein incorporated by reference); orchardgrass (Horn et al., *Plant Cell Rep.* 7:469, (1988), the entirety of which is herein incorporated by reference); rice (Toriyama et al., *Theor Appl. Genet.* 205:34, (1986); Park et al., *Plant Mol. Biol.*, 32:1135-1148, (1996); Abedinia et al., *Aust. J. Plant Physiol.* 24:133-141, (1997); Zhang and Wu, *Theor. Appl. Genet.* 76:835, (1988); Zhang et al., *Plant Cell Rep.* 7:379, (1988); Battraw and Hall, *Plant Sci.* 86:191-202, (1992); Christou et al., *Bio/Technology* 9:957, (1991), all of which the entirety is herein incorporated by reference); sugarcane (Bower and Birch, *Plant J.* 2:409, (1992), the entirety of which is herein incorporated by reference); tall fescue (Wang et al., *Bio/Technology* 10:691, (1992), the entirety of which is herein incorporated by reference), and wheat (Vasil et al., Bio/Technology 10:667, (1992), the entirety of which is herein incorporated by reference; U.S. Pat. No. 5,631,152, the entirety of which is herein incorporated by reference.

Assays for gene expression based on the transient expression of cloned nucleic acid constructs have been developed by introducing the nucleic acid molecules into plant cells by polyethylene glycol treatment, electroporation, or particle bombardment (Marcotte, et al., *Nature*, 335:454-457 (1988); Marcotte, et al., *Plant Cell*, 1:523-532 (1989); McCarty, et al., *Cell* 66:895-905 (1991); Hattori, et al., *Genes Dev.* 6:609-618 (1992); Goff, et al., *EMBO J.* 9:2517-2522 (1990), all of which are herein incorporated by reference in their entirety). Transient expression systems may be used to functionally dissect gene constructs (See generally, Mailga et al., *Methods in Plant Molecular Biology*, Cold Spring Harbor Press (1995)).

Any of the nucleic acid molecules of the present invention may be introduced into a plant cell in a permanent or transient manner in combination with other genetic elements such as vectors, promoters enhancers etc. Further any of the nucleic acid molecules of the present invention may be introduced into a plant cell in a manner that allows for over expression of the protein or fragment thereof encoded by the nucleic acid molecule.

Nucleic acid molecules of the present invention may be used in cosuppression. Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279-289 (1990); van der Krol et al., *Plant Cell* 2:291-299 (1990), both of which are herein incorporated by reference in their entirety). Cosuppression may result from stable transformation with a single copy nucleic acid molecule that is homologous to a nucleic acid sequence found with the cell (Prolls and Meyer, *Plant J.* 2:465-475 (1992), the entirety of which is herein incorporated by reference) or with multiple copies of a nucleic acid molecule that is homologous to a nucleic acid sequence found with the cell (Mittlesten et al., *Mol. Gen. Genet.* 244: 325-330 (1994), the entirety of which is herein incorporated by reference). Genes, even though different, linked to homologous promoters may result in the cosuppression of the linked genes (Vaucheret, C R. *Acad. Sci. III* 316: 1471-1483 (1993), the entirety of which is herein incorporated by reference).

This technique has, for example been applied to generate white flowers from red petunia and tomatoes that do not ripen on the vine. Up to 50% of petunia transformants that contained a sense copy of the chalcone synthase (CHS) gene produced white flowers or floral sectors; this was as a result of the post-transcriptional loss of mRNA encoding CHS (Flavell, *Proc. Natl. Acad. Sci. USA* 91:3490-3496 (1994)), the entirety of which is herein incorporated by reference). Cosuppression may require the coordinate transcription of the transgene and the endogenous gene, and can be reset by a developmental control mechanism (Jorgensen, *Trends Biotechnol,* 8:340344 (1990); Meins and Kunz, In: *Gene Inactivation and Homologous Recombination in Plants* (Paszkowski, J., ed.), pp. 335-348. Kluwer Academic, Netherlands (1994), both of which are herein incorporated by reference in their entirety).

It is understood that one or more of the nucleic acids of the present invention comprising SEQ ID NO:1 or complement thereof through SEQ ID NO: 69652 or complement thereof or fragment thereof or other nucleic acid molecules of the present invention, may be introduced into a plant cell and transcribed using an appropriate promoter with such transcription resulting in the co-suppression of an endogenous protein.

Nucleic acid molecules of the present invention may be used to reduce gene function. Antisense approaches are a way of preventing or reducing gene function by targeting the genetic material (Mol et al., *FEBS Lett.* 268:427-430 (1990), the entirety of which is herein incorporated by reference). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., *In Genetic Engineering*, Setlow (ed.), Vol. 11, New York: Plenum 49-63 (1989), the entirety of which is herein incorporated by reference).

The principle of regulation by antisense RNA is that RNA that is complementary to the target mRNA is introduced into cells, resulting in specific RNA:RNA duplexes being formed by base pairing between the antisense substrate and the target mRNA (Green et al., *Annu. Rev. Biochem.* 55:569-597 (1986), the entirety of which is herein incorporated by reference). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155-184 (1990), the entirety of which is herein incorporated by reference). An antisense vector is constructed by standard procedures and introduced into cells by transformation, transfection, electroporation, microinjection, or by infection, etc. The type of transformation and choice of vector will determine whether expression is transient or stable. The promoter used for the antisense gene may influence the level, timing, tissue, specificity, or inducibility of the antisense inhibition.

It is understood that protein synthesis activity in a plant cell may be reduced or depressed by growing a transformed plant cell containing a nucleic acid molecule of the present invention.

Antibodies have been expressed in plants (Hiatt et al., *Nature* 342:76-78 (1989); Conrad and Fielder, *Plant Mol. Biol.* 26:1023-1030 (1994), both of which are herein incorporated by reference in their entirety). Cytoplasmic expression of a scFv (single-chain Fv antibodies) has been reported to delay infection by artichoke mottled crinkle virus. Transgenic plants that express antibodies directed against endogenous proteins may exhibit a physiological effect (Philips et al., *EMBO J.* 16:4489-4496 (1997); Marion-Poll, *Trends in Plant Science* 2:447-448 (1997), both of which are herein incorporated by reference in their entirety). For example, expressed anti-abscisic antibodies reportedly result in a general perturbation of seed development (Philips et al., *EMBO J.* 16:4489-4496 (1997)).

Nucleic acid molecules of the present invention may be used as antibodies. Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313-1315 (1997); Baca et al., *Ann. Rev. Biophys. Biomol. Struct.* 26:461-493 (1997), both of which are herein incorporated by reference in their entirety). The catalytic abilities of abzymes may be enhanced by site directed mutagenesis. Examples of abzymes are, for example, set forth in U.S. Pat. No. 5,658,753; U.S. Pat. No. 5,632,990; U.S. Pat. No. 5,631,137; U.S. Pat. No. 5,602,015; U.S. Pat. No. 5,559,538; U.S. Pat. No. 5,576,174; U.S. Pat. No. 5,500,358; U.S. Pat. No. 5,318,897; U.S. Pat. No. 5,298,409; U.S. Pat. No. 5,258,289 and U.S. Pat. No. 5,194,585, all of which are herein incorporated in their entirety.

It is understood that any of the antibodies of the present invention may be expressed in plants and that such expression can result in a physiological effect. It is also understood that any of the expressed antibodies may be catalytic.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Mailga et al., *Methods in Plant Molecular Biology*, Cold Spring Harbor Press (1995); Birren et al., *Genome Analysis: Analyzing DNA,* 1, Cold Spring Harbor, N.Y. (1998), both of which are herein incorporated by reference in their entirety).

The nucleotide sequence provided in SEQ ID NO:1, through SEQ ID NO: 69652 or fragment thereof, or complement thereof, or a nucleotide sequence at least 90% identical, preferably 95%, identical even more preferably 99% or 100% identical to the sequence provided in SEQ ID NO:1 through SEQ ID NO: 69652 or fragment thereof, or complement thereof, can be "provided" in a variety of mediums to facilitate use fragment thereof. Such a medium can also provide a subset thereof in a form that allows a skilled artisan to examine the sequences.

In a preferred embodiment, 20, preferably 50, more preferably 100, even more preferably 1,000, 2,000, 3,000, or 4,000 of the nucleic acid sequences of the present invention can be provided in a variety of mediums.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g., text file or database) in order to obtain computer readable medium having recorded thereon the nucleotide sequence information of the present invention.

By providing one or more of nucleotide sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403-410 (1990)) and BLAZE (Brutlag et al., *Comp. Chem.* 17:203-207 (1993), the entirety of which is herein incorporated by reference) search algorithms on a Sybase system can be used to identify open reading frames (ORFs) within the genome that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif. A variety of known algorithms are disclosed publicly and a variety of commercially available software for conducting search means are available and can be used in the computer-based systems of the present invention. Examples of such software include, but are not limited to, MacPattern (EMBL), BLASTIN and BLASTIX (NCBIA). One of the available algorithms or implementing software packages for conducting homology searches can be adapted for use in the present computer-based systems.

The most preferred sequence length of a target sequence is from about 10 to 100 amino acids or from about 30 to 300 nucleotide residues. However, it is well recognized that during searches for commercially important fragments of the nucleic acid molecules of the present invention, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

Thus, the present invention further provides an input means for receiving a target sequence, a data storage means for storing the target sequences of the present invention sequence identified using a search means as described above, and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments sequence of the present invention. For example, implementing software which implement the BLAST and BLAZE algorithms (Altschul et al., *J. Mol. Biol.* 215:403-410 (1990)) can be used to identify open frames within the nucleic acid molecules of the present invention. A skilled artisan can readily recognize that any one of the publicly available homology search programs can be used as the search means for the computer-based systems of the present invention.

Having now generally described the invention, the same will be more readily understood through reference to the following examples which are provided by way of illustration, and are not intended to be limiting of the present invention, unless specified.

Example 1

BACs are stable, non-chimeric cloning systems having genomic fragment inserts (100-300 kb) and their DNA can be prepared for most types of experiments including DNA sequencing. BAC vector, pBeloBAC11, is derived from the endogenous *E. coli* F-factor plasmid, which contains genes for strict copy number control and unidirectional origin of DNA replication. Additionally, pBeloBAC11 has three unique restriction enzyme sites (Hind III, Bam HI and Sph I) located within the LacZ gene which can be used as cloning sites for megabase-size plant DNA. Indigo, another BAC vector contains Hind III and Eco RI cloning sites. This vector also contains a random mutation in the LacZ gene that allows for darker blue colonies.

As an alternative, the P1-derived artificial chromosome (PAC) can be used as a large DNA fragment cloning vector (Ioannou, et al., *Nature Genet.* 6:84-89 (1994); Suzuki, et al., *Gene* 199:133-137 (1997), both of which are herein incorporated by reference in their entirety). The PAC vector has most of the features of the BAC system, but also contains some of the elements of the bacteriophage P1 cloning system.

BAC libraries are generated by ligating size-selected restriction digested DNA with pBeloBAC11 followed by electroporation into *E. coli*. BAC library construction and characterization is extremely efficient when compared to YAC (yeast artificial chromosome) library construction and analysis, particularly because of the chimerism associated with YACs and difficulties associated with extracting YAC DNA.

There are general methods for preparing megabase-size DNA from plants. For example, the protoplast method yields megabase-size DNA of high quality with minimal breakage. The process involves preparing young leaves which are manually feathered with a razor-blade before being incubated for four to five hours with cell-wall-degrading enzymes. The second method developed by Zhange et al., *Plant J.* 7:175-184 (1995), the entirety of which is herein incorporated by reference, is a universal nuclei method that works well for several divergent plant taxa. Fresh or frozen tissue is homogenized with a blender or mortar and pestle. Nuclei are then isolated and embedded. DNA prepared by the nucleic method is often more concentrated and is reported to contain lower amounts of chloroplast DNA than the protoplast method.

Once protoplasts or nuclei are produced, they are embedded in an agarose matrix as plugs or microbeads. The agarose provides a support matrix to prevent shearing of the DNA while allowing enzymes and buffers to diffuse into the DNA. The DNA is purified and manipulated in the agarose and is stable for more than one year at 4° C.

Once high molecular weight DNA has been prepared, it is fragmented to the desired size range. In general, DNA fragmentation utilizes two general approaches, 1) physical shearing and 2) partial digestion with a restriction enzyme that cuts relatively frequently within the genome. Since physical shearing is not dependent upon the frequency and distribution of particular restriction enzymes sites, this method should yield the most random distribution of DNA fragments. However, the ends of the sheared DNA fragments must be repaired and cloned directly or restriction enzyme sites added by the addition of synthetic linkers. Because of the subsequent steps required to clone DNA fragmented by shearing, most protocols fragment DNA by partial restriction enzyme digestion. The advantage of partial restriction enzyme digestion is that no further enzymatic modification of the ends of the restriction fragments are necessary. Four common techniques that can be used to achieve reproducible partial digestion of megabase-size DNA are 1) varying the concentration of the restriction enzyme, 2) varying the time of incubation with the restriction enzyme 3) varying the concentration of an enzyme cofactor (e.g., $Mg^{2+}$) and 4) varying the ratio of endonuclease to methylase.

There are three cloning sites in pBeloBAC11, but only Hind III and Bam HI produce 5' overhangs for easy vector dephosphorylation. These two restriction enzymes are primarily used to construct BAC libraries. The optimal partial digestion conditions for megabase-size DNA are determined by wide and narrow window digestions. To optimize the optimum amount of Hind III, 1, 2, 3, 10, and 5-units of enzyme are each added to 50 ml aliquots of microbeads and incubated at 37° C. for 20 minutes.

After partial digestion of megabase-size DNA, the DNA is run on a pulsed-field gel, and DNA in a size range of 100-500 kb is excised from the gel. This DNA is ligated to the BAC vector or subjected to a second size selection on a pulsed field gel under different running conditions. Studies have previously reported that two rounds of size selection can eliminate small DNA fragments co-migrating with the selected range in the first pulse-field fractionation. Such a strategy results in an increase in insert sizes and a more uniform insert size distribution. A practical approach to performing size selections is to first test for the number of clones/microliter of ligation and insert size from the first size selected material. If the numbers are good (500 to 2000 white colony/microliter of ligation) and the size range is also good (50 to 300 kb) then a second size selection is practical. When performing a second size selection one expects a 80 to 95% decrease in the number of recombinant clones per transformation.

Twenty to two hundred nanograms of the size-selected DNA is ligated to dephosphorylated BAC vector (molar ratio of 10 to 1 in BAC vector excess). Most BAC libraries use a molar ratio of 5 to 15:1 (size selected DNA:BAC vector).

Transformation is carried out by electroporation and the transformation efficiency for BACs is about 40 to 1,500 transformants from one microliter of ligation product or 20 to 1000 transformants/ng DNA.

Several tests can be carried out to determine the quality of a BAC library. Three basic tests to evaluate the quality include: the genome coverage of a BAC library-average insert size, average number of clones hybridizing with single copy probes and chloroplast DNA content.

The determination of the average insert size of the library is assessed in two ways. First, during library construction every ligation is tested to determine the average insert size by assaying 20-50 BAC clones per ligation. DNA is isolated from recombinant clones using a standard mini preparation protocol, digested with Not I to free the insert from the BAC vector and then sized using pulsed field gel electrophoresis (Maule, *Molecular Biotechnology* 9:107-126 (1998), the entirety of which is herein incorporated by reference).

To determine the genome coverage of the library, it is screened with single copy RFLP markers distributed randomly across the genome by hybridization. Microtiter plates containing BAC clones are spotted onto Hybond membranes. Bacteria from 48 or 72 plates are spotted twice onto one membrane resulting in 18,000 to 27,648 unique clones on each membrane in either a 4×4 or 5×5 orientation. Since each clone is present twice, false positives are easily eliminated and true positives are easily recognized and identified.

Finally, the chloroplast DNA content in the BAC library is estimated by hybridizing three chloroplast genes spaced evenly across the chloroplast genome to the library on high density hybridization filters.

There are strategies for isolating rare sequences within the genome. For example, higher plant genomes can range in size from 100 Mb/1 C (*Arabidopsis*) to 15,966 Mb/C (*Triticum aestivum*), (Arumuganathan and Earle, *Plant Mol Bio Rep.* 9:208-219 (1991), the entirety of which is herein incorporated by reference). The number of clones required to achieve a given probability that any DNA sequence will be represented in a genomic library is $N=(\ln(1-P))/(\ln(1-L/G))$ where N is the number of clones required, P is the probability desired to get the target sequence, L is the length of the average clone insert in base pairs and G is the haploid genome length in base pairs (Clarke et al., *Cell* 9:91-100 (1976) the entirety of which is herein incorporated by reference).

The rice BAC library of the present invention is constructed in the pBeloBAC11 or similar vector. Inserts are generated by partial Eco RI or other enzymatic digestion of DNA. The 25× library provides 4-5× coverage sequence from BAC clones across genome.

Example 2

Two basic methods can be used for DNA sequencing, the chain termination method of Sanger et al., *Proc. Natl. Acad. Sci. USA* 74:5463-5467 (1977), the entirety of which is herein incorporated by reference and the chemical degradation method of Maxam and Gilbert, *Proc. Natl. Acad. Sci. USA* 74:560-564 (1977), the entirety of which is herein incorporated by reference. Automation and advances in technology such as the replacement of radioisotopes with fluorescence-based sequencing have reduced the effort required to sequence DNA (Craxton, *Methods*, 2:20-26 (1991); Ju et al., *Proc. Natl. Acad. Sci. USA* 92:4347-4351 (1995); Tabor and Richardson, *Proc. Natl. Acad. Sci. USA* 92:6339-6343 (1995), all of which are herein incorporated by reference in their entirety). Automated sequencers are available from, for example, Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

In addition, advances in capillary gel electrophoresis have also reduced the effort required to sequence DNA and such advances provide a rapid high resolution approach for sequencing DNA samples (Swerdlow and Gesteland, *Nucleic Acids Res.* 18:1415-1419 (1990); Smith, *Nature* 349:812-813 (1991); Luckey et al., *Methods Enzymol.* 218:154-172 (1993); Lu et al., *J. Chromatog. A.* 680:497-501 (1994); Carson et al., *Anal. Chem.* 65:3219-3226 (1993); Huang et al., *Anal. Chem.* 64:2149-2154 (1992); Kheterpal et al., *Electrophoresis* 17:1852-1859 (1996); Quesada and Zhang, *Electrophoresis* 17:1841-1851 (1996); Baba, Yakugaku Zasshi 117: 265-281 (1997), all of which are herein incorporated by reference in their entirety).

A number of sequencing techniques are known in the art, including fluorescence-based sequencing methodologies. These methods have the detection, automation and instrumentation capability necessary for the analysis of large volumes of sequence data. Currently, the 377 DNA Sequencer (Perkin-Elmer Corp., Applied Biosystems Div., Foster City, Calif.) allows the most rapid electrophoresis and data collection. With these types of automated systems, fluorescent dye-labeled sequence reaction products are detected and data entered directly into the computer, producing a chromatogram that is subsequently viewed, stored, and analyzed using the corresponding software programs. These methods are known to those of skill in the art and have been described and reviewed (Birren et al., *Genome Analysis: Analyzing DNA*, 1, Cold Spring Harbor, N.Y. (1999), the entirety of which is herein incorporated by reference).

PHRED is used to call the bases from the sequence trace files (on the Worldwide web at mbt.washington.edu). Phred uses Fourier methods to examine the four base traces in the region surrounding each point in the data set in order to predict a series of evenly spaced predicted locations. That is, it determines where the peaks would be centered if there were no compressions, dropouts, or other factors shifting the peaks from their "true" locations. Next, PHRED examines each trace to find the centers of the actual, or observed peaks and the areas of these peaks relative to their neighbors. The peaks are detected independently along each of the four traces so many peaks overlap. A dynamic programming algorithm is used to match the observed peaks detected in the second step with the predicted peak locations found in the first step.

After the base calling is completed, contaminating sequences (*E. coli*, BAC vector sequences>50 bases and sub-cloning vector are removed and constraints are made for the assembler. Contigs are assembled using CAP3 (Huang, et al., *Genomics* 46: 37-45 (1997) the entirety of which is herein incorporated by reference).

Example 3

This example illustrates the identification of combigenes within the rice genomic contig library as assembled in Example 2. The genes and partial genes embedded in such contigs are identified through a series of informatic analyses. The tools to define genes fall into two categories: homology-based and predictive-based methods. Homology-based searches (e.g., GAP2, BLASTX supplemented by NAP and TBLASTX) detect conserved sequences during comparisons of DNA sequences or hypothetically translated protein sequences to public and/or proprietary DNA and protein databases. Existence of an *Oryza sativa* gene is inferred if significant sequence similarity extends over the majority of the target gene. Since homology-based methods may overlook genes unique to *Oryza sativa*, for which homologous nucleic acid molecules have not yet been identified in databases, gene prediction programs are also used. Predictive methods employed in the definition of the *Oryza sativa* genes included the use of the GenScan gene predictive software program which is available from Stanford University (e.g. at the web site gnomic/stanford.edu/GENSCANW.html). GenScan, in general terms, infers the presence and extent of a gene through a search for "gene-like" grammar.

The homology-based methods used to define the *Oryza sativa* gene set included GAP2, BLASTX supplemented by NAP and TBLASTX. For a description of BLASTX and TBLASTX see Coulson, *Trends in Biotechnology* 12:76-80 (1994) and Birren et al., *Genome Analysis*, 1:543-559 (1997). GAP2 and NAP are part of the Analysis and Annotation Tool (AAT) for Finding Genes in Genomic Sequences which was developed by Xiaoqiu Huang at Michigan Tech University and is available at the web site genome.cs.mtu.edu/. The AAT package includes two sets of programs, one set DPS/NAP (referred to as "NAP") for comparing the query sequence with a protein database, and the other set DDS/GAP2 (referred to as "GAP2") for comparing the query sequence with a cDNA database. Each set contains a fast database search program and a rigorous alignment program. The database search program quickly identifies regions of the query sequence that are similar to a database sequence. Then the alignment program constructs an optimal alignment for each region and the database sequence. The alignment program also reports the coordinates of exons in the query sequence. See Huang, et al., *Genomics* 46: 37-45 (1997).

The GAP2 program computes an optimal global alignment of a genomic sequence and a cDNA sequence without penalizing terminal gaps. A long gap in the cDNA sequence is given a constant penalty. The DNA-DNA alignment by GAP2 adjusts penalties to accommodate introns. The GAP2 program makes use of splice site consensuses in alignment computation. GAP2 delivers the alignment in linear space, so long sequences can be aligned. See Huang, *Computer Applications in the Biosciences* 10 227-235 (1994). The GAP2 program aligned the *Oryza sativa* contigs with a library of *Oryza sativa* 25,384 cDNAs.

The NAP program computes a global alignment of a DNA sequence and a protein sequence without penalizing terminal gaps. NAP handles frameshifts and long introns in the DNA sequence. The program delivers the alignment in linear space, so long sequences can be aligned. It makes use of splice site consensuses in alignment computation. Both strands of the DNA sequence are compared with the protein sequence and one of the two alignments with the larger score is reported. See Huang, and Zhang, "*Computer Applications in the Biosciences* 12(6), 497-506 (1996).

NAP takes a nucleotide sequence, translates it in three forward reading frames and three reverse complement reading frames, and then compares the six translations against a protein sequence database (e.g. the non-redundant protein (i.e., nr-aa) database maintained by the National Center for Biotechnology Information as part of GenBank and available on the Worldwide web at ncbi.nlm.nih.gov).

The first homology-based search for genes in the *Oryza sativa* contigs is effected using the GAP2 program and the *Oryza sativa* library of clustered *Oryza sativa* cDNA. The *Oryza sativa* clusters are mapped onto an assembly of *Oryza sativa* contigs represented by SEQ ID NO. 1 through SEQ ID NO. 69652 using the GAP2 program. GAP2 standards for selecting a DNA-DNA match were ≧82% sequence identity with the following parameters:

gap extension penalty=1
match score=2
gap open penalty=6
gap length for constant penalty=20
mismatch penalty=−2
minimum exon length=21

When a particular *Oryza sativa* cDNA aligns to more than one *Oryza sativa* contig, the alignment with the highest identity is selected and alignments with lower levels of identity are filtered out as surreptitious alignments. *Oryza sativa* cDNA sequences aligning to *Oryza sativa* contigs with exceptionally low complexity were filtered out when the basis for alignment included a high number of cDNAs with poly A tails aligning to genomic regions with extended repeats of A or T.

The second homology-based method used for gene discovery is BLASTX hits extended with the NAP software package. BLASTX is run with the *Oryza sativa* genomic contigs represented by SEQ ID NO. 1 through SEQ ID NO. 69652 as queries against the GenBank non-redundant protein data library identified as "nr-aa". NAP is used to better align the amino acid sequences as compared to the genomic sequence. NAP extends the match in regions where BLASTX has identified high-scoring-pairs (HSPs), predicts introns, and then links the exons into a single ORF prediction. Experience suggests that NAP tends to mis-predict the first exon. The NAP parameters are:

gap extension penalty=1
gap open penalty=15
gap length for constant penalty=25
min exon length (in aa)=7
homology>30%

The NAP alignment score and GenBank reference number for best match are reported for each contig for which there is a NAP hit.

In the final homology-based method, TBLASTX, is used with cDNA information from three plant sequencing projects: 12,217 sequences from *Triticum aestivum*, 101,574 sequences from *Glycine max*, 113,242 sequences from *Zea mays* and 56,754 sequences from *Arabidopsis thaliana*. Conservative standards for inclusion of TBLASTX hits into the gene set are utilized. These standards are a minimal E value of 1E-20, and for terminal exons, a minimal match of 200 bp within the 1000 most 5' and 3' ends of an *Oryza sativa* contig.

The GenScan program is "trained" with *Arabidopsis thaliana* characteristics. Though better than the "off-the-shelf" version, the GenScan trained to identify *Oryza sativa* genes proved more proficient at predicting exons than predicting full-length genes. Predicting full-length genes is compromised by point mutations in the unfinished contigs, as well as by the short length of the contigs relative to the typical length of a gene. Due to the errors found in the full-length gene predictions by GenScan, inclusion of GenScan-predicted genes is limited to those genes and exons whose probabilities are above a conservative probability threshold. The GenScan parameters are:

weighted mean GenScan P value>0.4
mean GenScan T value>0
mean GenScan Coding score>50
length>200 bp
minimum TBLASTX E value<1E-20

The weighted mean GenScan P value is a probability for correctly predicting ORFs or partial ORFs and is defined as the $(1/\Sigma l_i)(\Sigma l_i P_i)$, where "l" is the length of a exon and "P" is the probability or correctness for the exon.

The gene predictions from these programs are stored in a database and then combigenes are derived from these predictions. A combigene is a cluster of putative genes which satisfy the following criteria: 1) all genes making up a single combigene are located on the same strand of a contig 2) individual genes have at least 100 bp overlap with each other 3) if an individual gene is predicted by NAP it has at least 30% sequence identity to its hit 4) if an individual gene is predicted by GAP2 it has at least 85% sequence identity to its hit 5) if an individual gene is predicted by Genscan the weighted average of the probabilities calculated for all of its exons is not less than 0.4. The gene boundaries of a Genscan-predicted gene are determined while taking into account only exons. Since TBLASTX-predicted genes are standless the combigene which is made up of such genes can be assigned a strand only if there is a gene in the cluster that was predicted by a strand-defining gene-predicting program.

TABLE 1

The data in Table 1 of U.S. application Ser. No. 09/620,392 filed Jul. 19, 2000, now abandoned, (the entirety of which is incorporated by reference herein) are ordered by contigs. The combination genes are grouped by DNA strand location and sorted by their start position. The putative genes that make up a separate combigene are sorted by their start position.

*Column Headings:
  Seq num
    Provides the SEQ ID NO. for the listed sequences.
  Seq id
    Arbitrarily assigned name for each contig.
  Gene No.
    Arbitrarily assigned number for a combigene.
  Start
    Indicates the start position of the combigene gene.
  End
    Indicates the end position of the combigene gene.
  Strand
    Indicates the strand location of the gene (+/−).
  Name
    Indicates an arbitrarily assigned gene name based on the method used to predict the gene.
  Method
    Indicates the gene-predicting program used. These programs are GenScan, AAT/NAP, AAT/GAP or TBLASTX.
  Start
    The start position of the putative gene making up a combigene as predicted by the particular gene-predicting program used.
  End
    The end position of the putative gene making up a combigene as predicted by the particular gene-predicting program used.
  Exons
    The location of the exons found within the gene as determined by the gene-predicting program (Method).
  Score
    The aat_nap score is reported by the NAP program in the AAT package. It is an alignment score in which each match and mismatch is scored based on the BLOSUM62 scoring matrix.
  GI
    Each sequence in the GENBANK public database is arbitrarily assigned a unique NCBI gi (National Center for Biotechnology Information GenBank Identifier) number. In this table, the NCBI gi number which is associated (in the same row) with a given contig or singleton refers to the particular GENBANK sequence which is the best match for that sequence.
  Description
    The Description column provides a description of the NCBI gi referenced in the "GI" column.

| | | | |
|---|---|---|---|
| Seq. No. | 60151 | Seq. ID | OJ000330_03.0419.C31 |
| Gene No. | 125363 | Strand | + |
| Start | 235 | End | 338 |
| Name | OJ000330_03.0419.C31.o1.gs | Method | GENSCAN |
| Start | 235 | End | 338 |
| GI | none | Score | .83 |
| Exons | 235 . . . 338 | | |
| Seq. No. | 60151 | Seq. ID | OJ000330_03.0419.C31 |
| Gene No. | 125364 | Strand | + |
| Start | 1044 | End | 3133 |
| Name | OJ000330_03.0419.C31.o1.np | Method | AAT/NAP |
| Start | 1044 | End | 3096 |
| GI | 1935918 | Score | 1050 |
| Exons | 1044 . . . 1113, 1824 . . . 3096 | | |
| GI Descrip. | (U93559) putative serine/threonine protein kinase [*Brassica rapa*] | | |
| Seq. No. | 60151 | Seq. ID | OJ000330_03.0419.C31 |
| Gene No. | 125364 | Strand | + |
| Start | 1044 | End | 3133 |
| Name | OJ000330_03.0419.C31.o2.gs | Method | GENSCAN |
| Start | 1679 | End | 3133 |
| GI | none | Score | .98 |
| Exons | 1679 . . . 3133 | | |
| Seq. No. | 60151 | Seq. ID | OJ000330_03.0419.C31 |
| Name | OJ000330_03.0419.C31.o1.tc | Method | TBLASTX:Cress |
| Start | 1994 | End | 2986 |
| GI | none | Score | 73 |

-continued

| | | | |
|---|---|---|---|
| Exons | 1994 ... 2077, 2008 ... 2058, 2095 ... 2229, 2096 ... 2230, 2230 ... 2481, 2234 ... 2497, 2629 ... 2826, 2630 ... 2827, 2894 ... 2986 | | |
| Seq. No. | 60151 | Seq. ID | OJ000330_03.0419.C31 |
| Gene No. | 125365 | Strand | – |
| Start | 4825 | End | 5019 |
| Name | OJ000330_03.0419.C31.o1.tm | Method | TBLASTX:Maize |
| Start | 2008 | End | 2992 |
| GI | none | Score | 129 |
| Exons | 2008 ... 2058, 2102 ... 2257, 2104 ... 2280, 2249 ... 2518, 2266 ... 2469, 2635 ... 2802, 2636 ... 2830, 2894 ... 2992 | | |
| Seq. No. | 60151 | Seq. ID | OJ000330_03.0419.C31 |
| Gene No. | 125365 | Strand | – |
| Start | 4825 | End | 5019 |
| Name | OJ000330_03.0419.C31.o1.ts | Method | TBLASTX:Soybean |
| Start | 2167 | End | 2527 |
| GI | none | Score | 89 |
| Exons | 2167 ... 2232, 2168 ... 2236, 2240 ... 2527, 2329 ... 2469 | | |
| Seq. No. | 60151 | Seq. ID | OJ000330_03.0419.C31 |
| Gene No. | 125365 | Strand | – |
| Start | 4825 | End | 5019 |
| Name | OJ000330_03.0419.C31.o2.ts | Method | TBLASTX:Soybean |
| Start | 2626 | End | 2986 |
| GI | none | Score | 261 |
| Exons | 2626 ... 2826, 2627 ... 2827, 2894 ... 2986 | | |
| Seq. No. | 60151 | Seq. ID | OJ000330_03.0419.C31 |
| Gene No. | 125365 | Strand | – |
| Start | 4825 | End | 5019 |
| Name | OJ0003330_03.0419.C31.01.tw | Method | TBLASTX:Wheat |
| Start | 2663 | End | 2992 |
| GI | none | Score | 192 |
| Exons | 2663 ... 2827, 2668 ... 2805, 2894 ... 2992 | | |
| Seq. No. | 60151 | Seq. ID | OJ000330_03.0419.C31 |
| Gene No. | 125365 | Strand | – |
| Start | 4825 | End | 5019 |
| Name | OJ000330_03.0419.C31.o3.gs | Method | GENSCAN |
| Start | 4825 | End | 5019 |
| GI | none | Score | .81 |
| Exons | 4825 ... 5019 -- | | |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07868149B2). An electronic copy of the "Sequence Listing" will also be available from the USPTO upon request and payment of the fee set forth in 37 CFR 1.19(b)(3).

We claim:

1. A substantially purified nucleic acid molecule comprising a nucleic acid sequence that shares between 100% and 90% sequence identity with SEQ ID NO: 60151, wherein said nucleic acid molecule encodes a serine/threonine protein kinase or fragment thereof.

2. A substantially purified nucleic acid molecule comprising a nucleic acid sequence that shares between 100% and 90% sequence identity with the nucleic acid sequence of SEQ ID NO: 60151 or the complete complement thereof.

3. The substantially purified nucleic acid molecule according to claim 2, wherein said nucleic acid molecule comprises a microsatellite sequence.

4. The substantially purified nucleic acid molecule according to claim 3, wherein said nucleic acid molecule comprises a region having a single nucleotide polymorphism.

5. The substantially purified nucleic acid molecule of claim 2, wherein said nucleic acid sequence shares between 100% and 95% sequence identity with the nucleic acid sequence of SEQ ID NO: 60151 or the complete complement thereof.

6. The substantially purified nucleic acid molecule of claim 5, wherein said nucleic acid sequence shares between 100% and 98% sequence identity with the nucleic acid sequence of SEQ ID NO: 60151 or the complete complement thereof.

7. The substantially purified nucleic acid molecule of claim 6, wherein said nucleic acid sequence shares between 100% and 99% sequence identity with the nucleic acid sequence of SEQ ID NO: 60151 or the complete complement thereof.

8. The substantially purified nucleic acid molecule of claim 7, wherein said nucleic acid sequence shares 100% sequence identity with the nucleic acid sequence of SEQ ID NO: 60151 or the complete complement thereof.

9. A substantially purified nucleic acid molecule comprising a fragment of about 100 to about 200 nucleotide residues of SEQ ID NO: 60151, wherein said nucleic acid molecule encodes a serine/threonine protein kinase.

10. The substantially purified nucleic acid molecule of claim 9, wherein said nucleic acid molecule comprises bases 1679 to 3133 of SEQ ID NO: 60151.

11. A substantially purified nucleic acid molecule comprising a nucleic acid sequence, wherein said nucleic acid sequence comprises bases 1824 to 3096 of SEQ ID NO: 60151.

12. A transformed plant comprising a nucleic acid molecule, wherein the nucleic acid molecule comprises a sequence that shares between 100% and 90% sequence identity with the nucleic acid sequence of SEQ ID NO: 60151 or the complete complement thereof.

13. The transformed plant of claim 12, wherein said plant is an *Orzya sativa* plant.

14. The transformed plant of claim 12, wherein the nucleic acid molecule comprises a fragment of about 100 to about 200 nucleotide residues of SEQ ID NO: 60151, and wherein said nucleic acid molecule encodes a serine/threonine protein kinase.

15. The transformed plant of claim 12, wherein the nucleic acid molecule comprises bases 1679 to 3133 of SEQ ID NO: 60151.

16. The transformed plant of claim 12, wherein the nucleic acid molecule comprises bases 1824 to 3096 of SEQ ID NO: 60151.

17. A transformed seed comprising a nucleic acid molecule, wherein the nucleic acid molecule comprises a sequence that shares between 100% and 90% sequence identity with the nucleic acid sequence of SEQ ID NO: 60151 or the complete complement thereof.

18. The transformed seed of claim 17, wherein the nucleic acid molecule comprises a fragment of about 100 to about 200 nucleotide residues of SEQ ID NO: 60151, and wherein said nucleic acid molecule encodes a serine/threonine protein kinase.

19. The transformed seed of claim 17, wherein the nucleic acid molecule comprises bases 1679 to 3133 of SEQ ID NO: 60151.

20. The transformed seed of claim 17, wherein the nucleic acid molecule comprises bases 1824 to 3096 of SEQ ID NO: 60151.

* * * * *